United States Patent
Zhukauskas et al.

(10) Patent No.: US 8,007,533 B2
(45) Date of Patent: Aug. 30, 2011

(54) PROGRESSIVE GRIP ASSEMBLED BONE-TENDON-BONE GRAFTS, METHODS OF MAKING, AND METHODS OF USE

(75) Inventors: Arunas A. Zhukauskas, Gainesville, FL (US); Todd E. Goede, Alachua, FL (US); Eric J. Schmitt, Gainesville, FL (US); Lauren M. Brown, Gainesville, FL (US); Guy B. Grover, Gainesville, FL (US); Predrag Bursac, Gainesville, FL (US); Ben R. Sanders, Alachua, FL (US)

(73) Assignee: RTI Biologics, Inc., Alachua, FL (US)

( * ) Notice: Subject to any disclaimer, the term of this patent is extended or adjusted under 35 U.S.C. 154(b) by 754 days.

(21) Appl. No.: 11/674,084

(22) Filed: Feb. 12, 2007

(65) Prior Publication Data

US 2008/0195204 A1  Aug. 14, 2008

(51) Int. Cl.
*A61F 2/08* (2006.01)
(52) U.S. Cl. .................. 623/13.14; 623/13.17
(58) Field of Classification Search ...... 623/13.11–13.2, 623/13.14, 13.17
See application file for complete search history.

(56) References Cited

U.S. PATENT DOCUMENTS

| | | | |
|---|---|---|---|
| 5,108,431 A | 4/1992 | Mansat et al. | |
| 5,370,662 A | 12/1994 | Stone et al. | |
| 5,951,560 A | 9/1999 | Simon et al. | |
| 5,961,520 A | 10/1999 | Beck, Jr. et al. | |
| 6,482,584 B1 | 11/2002 | Mills et al. | |
| 6,497,726 B1 | 12/2002 | Carter et al. | |
| 6,554,862 B2 * | 4/2003 | Hays et al. | 623/13.14 |
| 6,730,124 B2 | 5/2004 | Steiner | |
| 7,001,430 B2 | 2/2006 | Mills et al. | |
| 7,131,994 B2 | 11/2006 | Mills et al. | |
| 2002/0072806 A1 * | 6/2002 | Buskirk et al. | 623/23.51 |

(Continued)

FOREIGN PATENT DOCUMENTS

| | | |
|---|---|---|
| EP | 1 297 799 | 4/2003 |
| WO | WO 9822047 A1 * | 5/1998 |
| WO | WO 99/44544 | 9/1999 |
| WO | WO 03/051236 | 6/2003 |
| WO | WO 2006/108114 | 10/2006 |

OTHER PUBLICATIONS

Frank R. Noyes, M.D., David L. Butler, Ph.D., Edward S. Grood, Ph.D., Ronald F. Zernicke, Ph.D. and Mohamed S. Hefzy, Ph.D., "Biomechanical Analysis of Human Ligament Grafts used in Knee-Ligament Repairs and Reconstructions", The Journal of Bone and Joint Surgery, vol. 66-A, No. 3, Mar. 1984, pp. 344-352.

(Continued)

*Primary Examiner* — Thomas J Sweet
*Assistant Examiner* — Megan Wolf
(74) *Attorney, Agent, or Firm* — McAndrews, Held & Malloy, Ltd.

(57) ABSTRACT

The present technology is related to the field of bone-tendon-bone implants, grafts, and components thereof, for implantation in mammals, particularly for implantation in humans. More particularly, the present technology relates to assembled implants that comprise a length of tendon and at least two bone components or intermediate bone blocks that are assembled to form a bone-tendon-bone implant, and methods of making such implants. In some embodiments, implants of the present technology provide a first grip on the tendon prior to implantation and a second grip during or after implantation. In some embodiments, bone block assemblies or intermediate bone blocks of the present technology have a first geometric configuration prior to implantation and a second geometric configuration during or after implantation.

39 Claims, 15 Drawing Sheets

U.S. PATENT DOCUMENTS

| | | | |
|---|---|---|---|
| 2003/0023304 | A1 | 1/2003 | Carter et al. |
| 2004/0030385 | A1* | 2/2004 | Steiner ........................ 623/13.14 |
| 2004/0115172 | A1 | 6/2004 | Bianchi et al. |
| 2006/0200235 | A1 | 9/2006 | Bianchi et al. |
| 2006/0200236 | A1 | 9/2006 | Bianchi et al. |
| 2006/0212036 | A1 | 9/2006 | Bianchi et al. |
| 2006/0229722 | A1 | 10/2006 | Bianchi et al. |
| 2006/0271192 | A1 | 11/2006 | Olsen et al. |

OTHER PUBLICATIONS

Dr. Seth Gasser and Dr. Renny Uppal, "Anterior Cruciate Ligament Reconstruction: A New Technique for Achilles Tendon Allograft Preparation", Arthroscopy: The Journal of Arthroscopic and Related Surgery, vol. 22, No. 12, Dec. 2006, pp. 1365.e1-1365e3.

International Search Report Corresponding to International Application Serial No. PCT/US2008/051472, mailed Sep. 30, 2008, 7 pages.

Written Opinion of the International Searching Authority corresponding to International Application Serial No. PCT/US2008/051472, mailed Sep. 30, 2008, 12 pages.

International Preliminary Report on Patentability for PCT Application Serial No. PCT/US2008/051472 filed Jan. 18, 2008.

Office Action, signed by Robilyn VanOs, issued on Oct. 1, 2010 in view of Canadian Application No. 2,678,236, pp. 1-3.

* cited by examiner

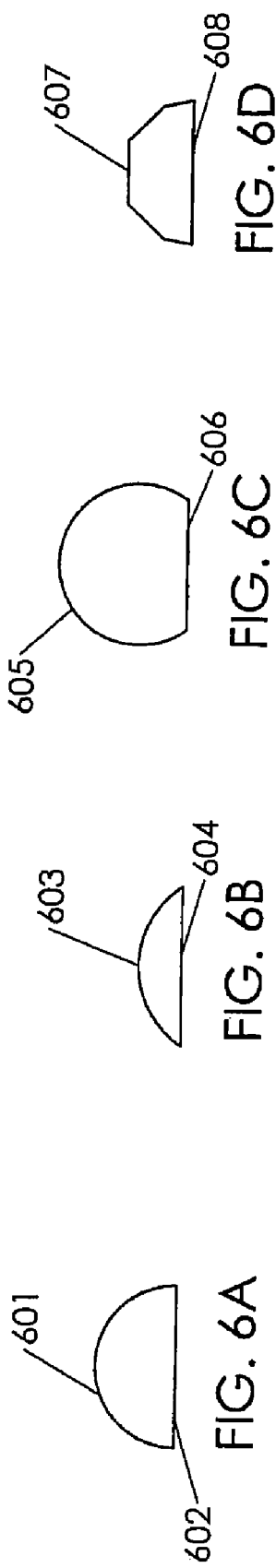

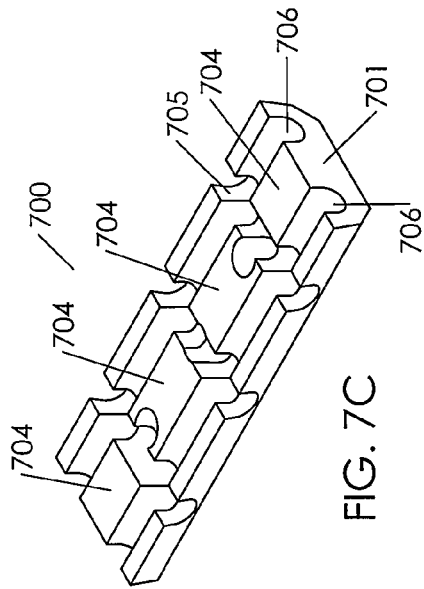
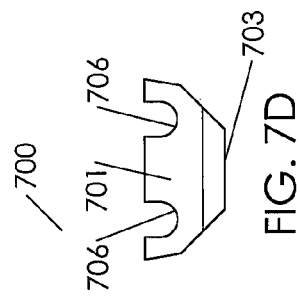
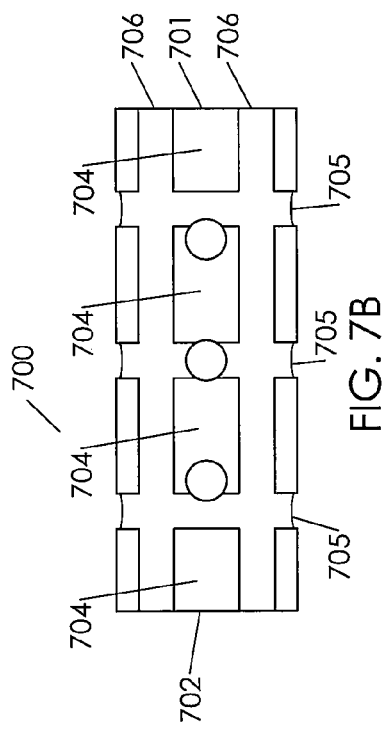
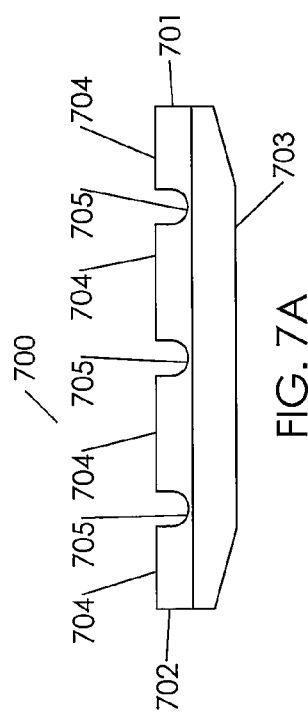

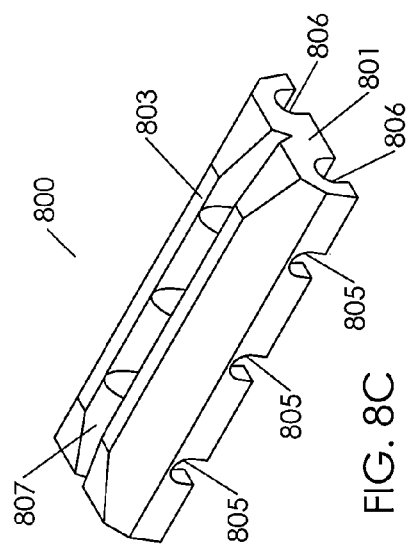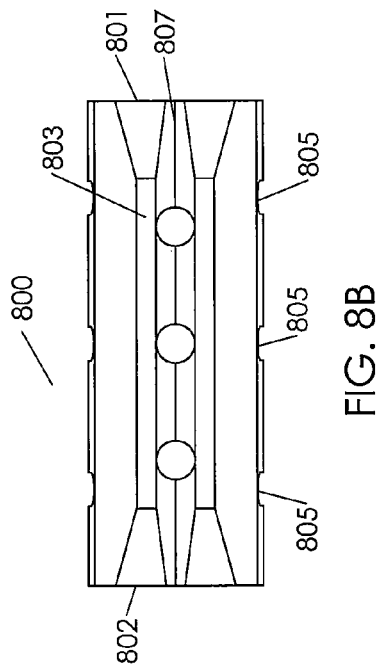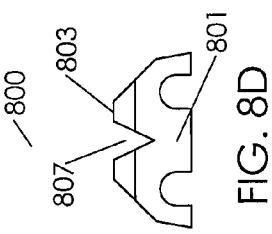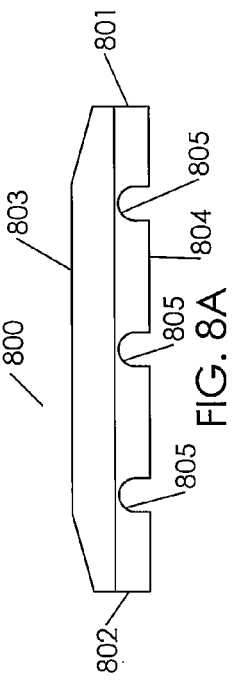

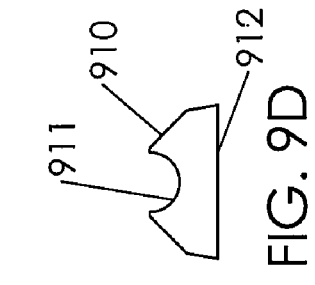
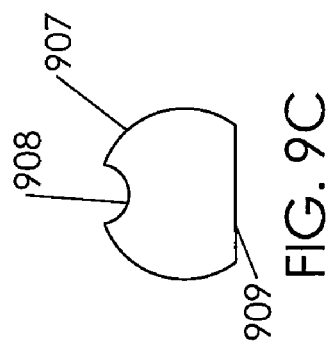
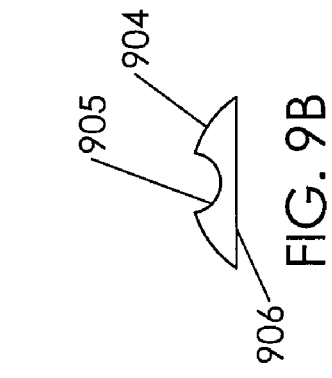
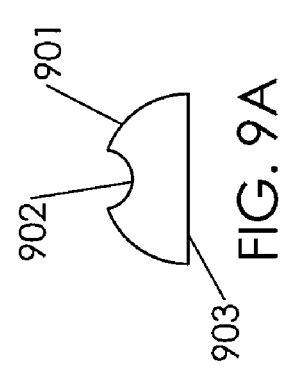
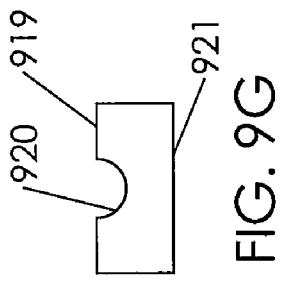
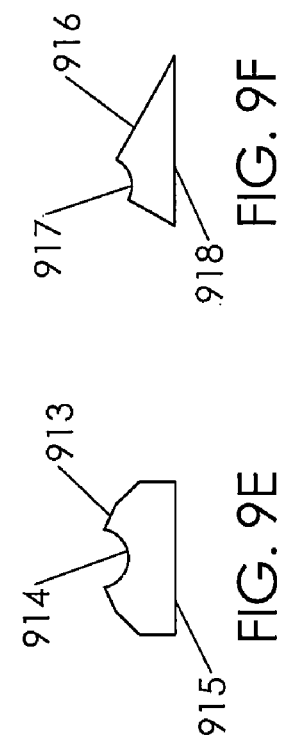
FIG. 9A FIG. 9B FIG. 9C FIG. 9D FIG. 9E FIG. 9F FIG. 9G

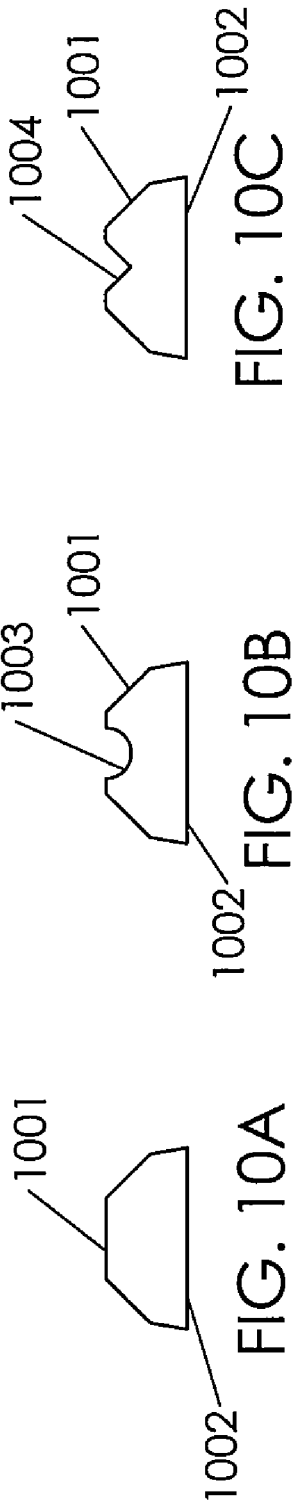
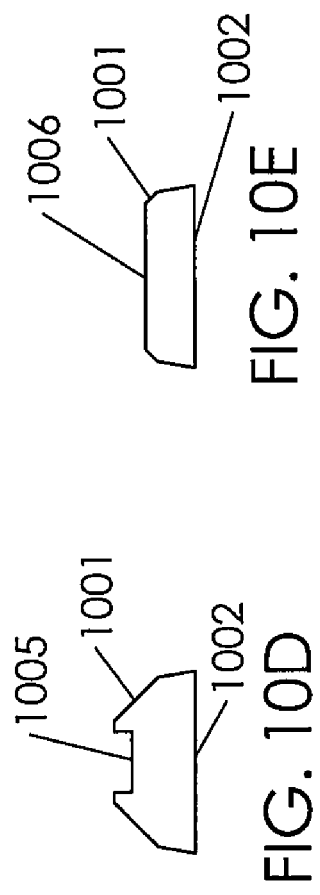

SECTION A-A

PROGRESSIVE GRIP ASSEMBLED BONE-TENDON-BONE GRAFTS, METHODS OF MAKING, AND METHODS OF USE

RELATED APPLICATIONS

Not Applicable

FEDERALLY SPONSORED RESEARCH OR DEVELOPMENT

Not Applicable

MICROFICHE/COPYRIGHT REFERENCE

Not Applicable

FIELD OF THE INVENTION

The present technology generally relates to the field of bone-tendon-bone implants, grafts, and components thereof, for implantation in mammals, particularly for implantation in humans.

BACKGROUND OF THE INVENTION

In the field of medicine, there has been an increasing need to develop implant materials for correction of biological defects. Particularly, in the field of orthopedic medicine, there has been the need to replace or correct bone, ligament and tendon defects or injuries. For example, Anterior cruciate ligament (ACL) reconstruction has become a common orthopedic procedure, with more than 200,000 ACL reconstructions being performed annually in the United States. The number of procedures involving the replacement, repair, or reconstruction of other tendons and ligaments is also increasing.

As a result, there have been development efforts relating to implants and implant materials to be used in such procedures. It is generally recognized that for implant materials to be acceptable, they must be pathogen free, and must be biologically acceptable. Some examples of synthetic implant materials include, but are not limited to, metals and polymeric substances. Some examples of non-synthetic implant materials include, but are not limited to, bone and soft tissues such as tendons and ligaments. Non-synthetic materials can be obtained from autogenic sources, allogenic sources, and xenogenic sources. The use of autograft, allograft, and xenograft bone in implants is generally desirable because these implant materials may be remodeled over time such that autogenous bone replaces the implant materials.

One way that the goal of having the bone components of an implant be remodeled over time can be achieved is by utilizing autograft bone, which is taken from a healthy harvest site within the patient and then implanted into a diseased or injured site within the same patient. However, use of autograft materials is attended by the significant disadvantage that a second site of morbidity must be created to harvest autograft for implantation into the diseased or injured site. Patients often complain about the pain and resultant effects at the harvest site. Additionally, the use of autograft materials increases procedure time and operation costs, as well as increasing the physician risk due to the handcrafting and judgment oriented aspects involved in harvesting and shaping an implant in the operating room.

In view of the disadvantages associated with the use of autograft implant materials, allograft and xenograft implant materials have been given increasing attention in recent years. Allograft materials are materials that are transplanted from genetically nonidentical individuals of the same species. For example, human allograft materials are generally recovered from cadavers and are then treated to remove pathogens prior to being implanted into live patients. Human allograft materials have the disadvantage of being frequently low in availability and high in cost of recovery, treatment and preparation for implantation. Certain highly desirable tissue types such as tendon allografts in general and bone-tendon or bone-tendon-bone grafts in particular face long standing and significant supply shortages. Demand for such tissues is difficult to measure definitively, but is believed to be at least about two to three times historically available levels of supply. Xenograft implant materials are materials that are transplanted from an animal of one species to an animal of another species. For example, bovine bone and porcine bone are two types of preferred xenograft materials for use in human patients. Such xenograft materials are readily available, but the actual use of such materials is significantly constrained due to immunological, regulatory, and disease transmission considerations and restrictions. Further, due to differences in size, structure and anatomy between species, it is sometimes difficult to locate a properly suited xenograft bone-tendon-bone implant.

In view of the foregoing considerations, it remains the case that there has been a long felt need for increased supplies of biologically acceptable implant materials to replace or correct bone, ligament and tendon defects or injuries. The present technology provides a significant advance in the art, and largely meets this need, by providing materials and methods for production of various bone-soft tissue implants from component parts to produce assembled implants.

Orthopedic medicine is increasingly becoming aware of the vast potential and advantages of using bone-tendon-bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting other tendons within the patient's own leg to provide increased support to a damaged knee. One shortcoming of such procedures involving reconnection or redirection of tendons is that the repaired joint tends to lack flexibility and stability.

The recent utilization of bone-tendon-bone grafts has dramatically improved the results of joint repair in cases of severe trauma. Even in cases of extensive damage to the joint ligaments, orthopedic surgeons have been able to achieve up to 100 percent range of motion and stability using donor bone-tendon-bone grafts. The term bone-tendon-bone graft, sometimes also referred to as a BTB, is used for historical reasons. By definition a "tendon" is a collagenous cord that attaches muscle to its point of origin, typically to bone, and a "ligament" is a band of collagenous tissue that interconnects bone or supports viscera. Thus, it would appear that a BTB would more properly be called a bone-ligament-bone graft or implant. However, many BTBs employ a tendon, which is larger and generally more plentiful in a body. One such example is a bone-patellar tendon-bone graft, also called a BPTB, which utilizes the patellar tendon Additionally, an implant using metal, polymeric, other synthetic, or artificial bone material at either end, instead of bone, may still be referred to as being a BTB or bone-tendon-bone graft in some cases. The name bone-soft tissue graft thus more accurately encompasses the subject matter meant when the term bon-tendon-bone graft is used. Because the name BTB became adopted by the art, it is used herein to encompass all of the bone-soft tissue-bone and bone-soft tissue grafts described herein.

Despite the realized advantages associated with bone-tendon-bone grafts, there have been some difficulties encountered with utilizing currently available bone-tendon-bone grafts.

For example, U.S. Pat. No. 5,370,662 ("the '662 patent"), entitled "Suture Anchor Assembly," which issued to Stone on Dec. 6, 1994, discloses the use of a screw made from titanium, stainless steel, or some other durable, non-degradable, biocompatible material having an eyelet at one end for attaching a suture connected to a soft material, such as a ligament or tendon. U.S. Pat. No. 5,370,662 at col. 1, lines 8-9. One problem with such a device is that the screw, although biocompatible, will never become assimilated into the patient's body and will not be remodeled over time. A second problem is that the tendon or ligament will never form a natural attachment to the screw.

One attempt at solving these problems was disclosed in U.S. Pat. No. 5,951,560 ("the '560 patent"), entitled "Wedge Orthopedic Screw," which issued on Sep. 14, 1999 to Simon et al. The '560 patent discloses a wedge-shaped interference screw made from a biocompatible material for use with a ligament and with two bone blocks for performing anterior cruciate ligament (ACL) repairs. In the '560 patent, a biocompatible, wedge-shaped interference screw, a bone block and a ligament are inserted into an osseous tunnel drilled into a bone of a patient in need of a ligament repair. The interference screw compresses the flat surface of a bone block against a ligament that is pressed into the wall of the osseous tunnel. As the interference screw advances, the force that it presses against the ligament is buttressed by the force against the opposing tunnel wall. A second interference screw compresses a second bone block against an opposing end of the ligament in a second osseous tunnel drilled in a second bone in need of ligament repair. One shortcoming of this approach is that it is difficult to pull a predetermined tension on the tendon because the tendon slips in the bone tunnel and uncontrollably alters the tension when the interference screw is being threaded in the bone tunnel. The slippery ligament is also subject to slippage when compressed between the bone block and the tunnel wall. Such slippage results in a loss of tension in the joint. In the case of an ACL repair, this loss of tension causes a wobbly knee. A second shortcoming of this method is an increase in complexity, difficulty, and time required during implantation, as the components are not pre-attached and do not have any predetermined position along the length of the tendon prior to implantation. This is undesirable in any human, and particularly in athletes.

Another approach to making a BTB is disclosed in U.S. Pat. No. 5,961,520 ("the '520 patent"), entitled "Endosteal Anchoring Device for Urging a Ligament Against a Bone," which issued to Beck, et al. on Oct. 5, 1999. Like the '560 patent, the '520 patent utilizes an interference screw and a bone block (called an "anchor body" therein) to press the end of a ligament against the side wall of an osseous tunnel in the patient's bone. The '520 patent differs from the '560 patent in that the ligament loops around the bone block in a "U" shape. This "U" shape of the tendon captures the tendon in the first bone tunnel, but leaves two free tendon ends to be secured in the second bone tunnel. In addition in the '520 patent, the bone block, which presses the ligament against the walls of the osseous tunnel contains two grooves for "locking" (col. 7, line 2) the ligament in place, and "restricting excessive compression on the ligament" (col. 7, lines 5-9). The "locking" of the tendon against the tunnel wall still leaves the tendon free to move against the tunnel wall near the ends of the anchor body. This can lead to impaired healing and recovery due to tendon to bone contact within the tunnel and also due to micromotions of the tendon within the tunnel. Ultimately, this may lead to widening of the bone tunnels rather than their closure. Additionally, the location of the tendon in the locking grooves is a function of the anchor body design and is not a controlled design parameter. Thus, the tendon placement with respect to either the tunnel wall or the tunnel centerline cannot be matched to particular surgical needs or to surgeon preference. Further, there is an increase in complexity, difficulty, and time required during implantation, as the components are not pre-attached and do not have any predetermined position along the length of the tendon prior to implantation.

Another approach to making a BTB is disclosed in U.S. Pat. No. 6,730,124 (the "'124 patent"), entitled "Bone-Tendon-Bone Assembly With Cancellous Allograft Bone Block," which issued on May 4, 2004 to Steiner. The '124 patent is directed toward a cancellous bone block assembly with at least one tendon replacement member being extended between two cancellous bone blocks. Each substantially cylindrically shaped cancellous bone block has a central through going bore, a flat exterior longitudinal surface and a channel longitudinally cut in the exterior of the bone block body opposite the flat longitudinal surface. The tendon replacement member is inserted through the central through going bore around the end of the block and looped back along the flat longitudinal side where it is tied to the back of the tendon loop. A channel cut in the exterior surface is adapted to receive an interference screw to keep the block anchored in a bone tunnel previously cut in the respective bone. One shortcoming of this design is the very large amount of contiguous cancellous bone required to construct the bone blocks. Cancellous bone material is costly, as well as being in high demand and short supply. The hollow cylindrical geometry of a single bone block having a diameter from 8-12 mm and a length of 25-35 mm (See '124 Patent at Col. 7, lines 8-10) requires that a very large piece of bone be drilled out and cut down to make each bone block. A second shortcoming with this approach is that the through going bore cut through the bone block to accommodate the tendon limits the wall thickness of cancellous bone. The thickness of the cancellous bone wall in the end bone block is also limited by the need for the bone block to fit into a bone tunnel with the tendon also looped next to the bone block. This presents a conflict between the need to maintain the size of the bone tunnel drilled in the patient's leg, the need to provide a large enough tendon to support the loads required for successful recovery and physical therapy, and the need to provide sufficient cancellous material for structural support and fixation. Another shortcoming of this system is the relatively low pullout strength supported by the looped and sutured configuration of the '124 patent. For example, the '124 patent recites 200 Newtons as a minimum pull out force ('124 patent at Col. 8, lines 37-38) and only two of the thirteen implants reported in the testing had a failure load greater than 400 Newtons. In contrast, an article published in 1984 by Noyes et. al., entitled "Biomechanical Analysis of Human Ligament Grafts Used In Knee-Ligament Repairs and Reconstructions," reported that failure loads of at least 445 Newtons are required of a reconstructed ACL during completion of normal activities of daily living. The Journal of Bone and Joint Surgery, Vol. 66-A, No. 3 (March 1984), pp. 344-352. Accordingly, it is desirable to provide implants that have an average strength (pull out failure load) of at least about 445 Newtons.

Yet another approach to making a BTB is disclosed in commonly assigned U.S. Pat Appl. Pub. No. 2003/0023304 ("the '304 publication"), to Carter et al., which published on Jan. 30, 2003. The '304 publication discloses several embodiments of a BTB. In each of the various embodiments, a tendon is bound in an internal chamber created in the bone blocks. For example, in FIG. 10 a plurality of cams reverse the direction of the tendon several times and cancellous chips packed in any open space bite into the tendon to keep it from slipping. In FIG. 12, a screw compresses the tendon against the side of an internal chamber. In FIG. 14, an internal wedge that has teeth bites into a tendon and tightens the grip as the tendon is pulled. In yet another embodiment, shown in FIG. 15, one end of a tendon is doubled over and the doubled over end is held in place by a series of grooves and rings. While all of these embodiments are potentially useful, they each are challenging to manufacture and/or assemble due to their inherent complexity and reliance on small or intricate parts.

One isolated and purified BTB that is not hindered by slippage or cut fibers when subjected to high tensile pulling is disclosed in commonly assigned U.S. Pat. No. 6,497,726 ("the '726 patent") which issued on Dec. 24, 2002 to Carter et al. The '726 patent discloses the use of natural bone-tendon attachments that are cut from allograft or xenograft sources, commonly referred to as "pre-shaped" or "natural" BTBs. Typically, the BTB is cut as a single piece from a section of the patella (bone), patellar tendon and the tibia (bone) of the donor. The availability of such implants can be limited due to the limited quantity of undamaged material sources and the age requirements that are acceptable to physicians. Generally, only 2-3 grafts can be obtained per knee of the donor, depending upon the donor's age and health. In utilizing pre-shaped (natural) BTBs, some of the physical dimensions of the graft, particularly tendon length, are determined by the anatomy of the donor. Frequently, this leads to compromises such as excessive gauge length (length between the bone blocks), which result in surgical challenges and compromised healing and recovery. For example, a natural BTB with a tendon that is too long for an ACL repair results in having a length of unsecured and wobbling tendon in the bone tunnel between the ends of the secured bone portions. The wobbling tendon hinders healing in the bone tunnel.

A recent development in making BTBs was published by Dr. Seth Gasser and Dr. Reuny Uppal in "Anterior Cruciate Reconstruction: A New Technique for Achilles Tendon Allograft Preparation," Arthroscopy: The Journal of Arthroscopic and related Surgery, Vol. 22, No. 12 (December 2006): pp. 1365.e1-1365.e3. Drs. Gasser and Uppal disclose the formation of a bone-Achilles' tendon-bone allograft by using an Achilles' allograft, which typically includes a block of calcaneus and the attached Achilles' tendon. The bone block with the natural tendon attachment used as the femoral end of the graft construct. A 25 mm long bone plug is harvested from the calcaneus with the attached Achilles' tendon. A free (unattached to the tendon) bone plug is then harvested from the remaining calcaneal bone block that measures 9 mm in diameter and 30 mm long. Three holes are drilled into the free bone plug, and the holes are used to suture the free bone plug to one side of the tendon on the tibial end of the graft construct. The formed graft is implanted and secured with interference screws in a similar fashion to a traditional bone-patellar tendon-bone ACL reconstruction. The making of BTB implants in this manner increases time spent in the operating room per procedure, which increases procedure costs, and can result in increased surgeon risk due to the fact that the surgeon is individually handcrafting each implant.

Accordingly, there is a need in the art for implants that provide a bone-tendon-bone graft that is consistently constructed to precise dimensions and is adapted for robust fixation, while allowing adherence to preferred surgical techniques. There is a further need for implants that promote reduced operating room times and reduce opportunities for error during surgery.

BRIEF SUMMARY OF THE INVENTION

The present technology relates to bone-tendon and bone-tendon-bone grafts or implants, also referred to herein as BTBs, as well as to methods of making such implants. More particularly, the present technology relates to assembled implants that comprise a length of tendon and at least two bone components or intermediate bone blocks that are assembled to form a BTB.

As discussed above, because the name bone-tendon-bone graft, or BTB, has become adopted by the art, it is used herein to encompass all of the bone-soft tissue-bone and bone-soft tissue grafts described herein. The term bone graft is generally defined in the 26$^{th}$ Edition of Stedman's Medical Dictionary (©1995) as being bone transplanted from a donor site to a recipient site. The term implant in the same reference is defined as being material inserted or grafted into tissues, and also as being a metallic or plastic device employed in joint reconstruction in orthopedics. However, the terms graft, bone-tendon graft, bone-tendon-bone graft, BTB, and implant are used herein in referring to devices of the present technology without regard to the material from which the devices are made, and should be understood as generally encompassing devices comprising metals, synthetic materials, non-synthetic (natural) materials, artificial bone, natural bone, or both.

The terms graft and implant are used interchangeably herein, and both should be understood as comprising materials from one location or source that are inserted as a unit into the body of a patient in need of such a graft or implant. In the case of synthetic materials, the synthetic materials would be manufactured and then provided for implantation into a patient. In the case of autograft materials, this refers to materials that are harvested from one site within the patient and transplanted to a different site within the same patient. In the case of allograft or xenograft materials, this refers to materials that are recovered from a donor and implanted into the patient.

The term "tendon" is used herein to refer to a length of tendon, a bundle of tendons of the same or different lengths, a length of ligament, a bundle of ligaments of the same length or different lengths, a segment or segments of pericardium, dermis or fascia, dura, skin, submucosal tissue (e.g., intestinal tissue), cartilage, other natural materials, synthetic materials, or a combination thereof. It is also within the scope of the present technology that the tissues in bundles are of the same thickness or of different thicknesses. In bundles, the tissues can be allograft, xenograft, synthetic, artificial ligament scaffolds or a combination thereof In at least some preferred embodiments, tendons of the present technology comprise autograft, allograft or xenograft materials.

The term bone component as used herein encompasses a component made of non-synthetic and/or synthetic materials. In at least some preferred embodiments, bone components of the present technology comprise autograft, allograft or xenograft bone. In other embodiments, bone components of the present technology comprise artificial bone, synthetic bone materials or polymeric bone substitute materials.

Embodiments of BTB grafts, and components of BTB grafts, of the present invention are typically made from components that are autograft, allograft or xenograft. While autograft is the most immunologically acceptable material, its use necessitates an additional trauma to the patient which makes its use less acceptable. From a regulatory point of view, allograft material is preferred. From the perspective of relative abundance, xenograft material is preferred. From the perspectives of strength, machinability and cost, metal or ceramic materials are preferred. From the perspective of manufacturability and some degree of biocompatibility, synthetic polymer materials are preferred. From the perspective of enhanced biocompatibility and biomimetics, synthetic inorganic materials such as polymer or carbon nanofibers are preferred. When a BTB of the present invention is assembled from natural materials, it is within the scope of the present invention that it be constructed from autograft, allograft, xenograft or a combination of these. When a BTB of the present invention is assembled from synthetic materials, it is within the scope of the present invention that it be constructed from metals, ceramics, synthetic polymers, synthetic inorganics, or a combination of these. It is further contemplated within the scope of the present invention that a graft be assembled from any combination of autograft, allograft or xenograft tissue components, together with any combinations of metals, ceramics, or synthetic polymers. In one such embodiment for use in humans, the pins used to assemble the bone blocks are ceramic, the bone segments used to form the intermediate bone blocks are machined from xenograft bone and the tendon portion is preshaped from a recovered xenograft or allograft tendon.

It is also within the scope of the invention that the bone components used in implants of the present technology may be made of artificial bone, by which is meant natural or synthetic materials including metals, ceramics polymers, composites or combinations thereof which exhibit properties similar to cortical bone. Commonly known examples are Poly L-Lactic Acid (PLLA) or calcium phosphate or hydroxyapatite based materials. These are available from various manufacturers such as U.S. Biomaterials, Alachua, Fla. and Osteo-Biologics, Inc. (OBI), San Antonio, Tex. Artificial or natural bone constructs may also be enhanced by the addition of cultured autologous or allograft or xenograft cells or genetically modified cells which support bone growth and healing by the presence of or expression of growth factors, hormones, or cell lines involved in the healing process. Any cells added to the artificial or natural bone constructs may be selected, treated, genetically modified, processed or otherwise engineered to reduce negative effects such as antigencity, inflammation, rejection, or immune response by or against the host.

The term intermediate bone block is used herein to refer to a type of bone component that is used as one piece in a multi-piece assembly that is referred to herein as a bone block assembly or an assembled bone block. In preferred embodiments, a bone block assembly or an assembled bone block of the present technology comprises at least two intermediate bone blocks.

It has been surprisingly discovered that assembled implants that grip a tendon can have improved performance when they are designed and configured such that the nature of the grip on the tendon changes from its pre-implantation state to its post-implantation state, while the general location and orientation of the bone block assemblies relative to the tendon is maintained at about the same position in at least one dimension. Accordingly, in one aspect, the present technology relates to an implant comprising a tendon and a bone block assembly comprising at least a first intermediate bone block and a second intermediate bone block, wherein the bone block assembly has a first grip on the tendon prior to implantation of the implant into a patient and a second grip on the tendon after implantation of the implant into a patient.

In some embodiments of the present technology, an implant is provided that comprises a tendon and a bone block assembly. The tendon has a length, and along its length, the tendon comprises at least a first end, a first intermediate section, a central section, a second intermediate section, and a second end. The bone block assembly comprises at least a first intermediate bone block and a second intermediate bone block. The bone block assembly has a first grip on the tendon prior to implantation of the implant into a patient and a second grip on the tendon after implantation of the implant into a patient. In at least one preferred embodiment, the tendon is secured between the first intermediate bone block and the second intermediate bone block at a fixed location along its length at the first end or at the first intermediate section of the tendon.

In at least one particularly preferred embodiment, the present technology provides an implant comprising a first bone block assembly at a first end of the implant, a second bone block assembly at a second end of the implant, and a tendon having a length, wherein the tendon comprises along its length at least a first end, a first intermediate section, a central section, a second intermediate section, and a second end. In such embodiments, the first bone block assembly comprises at least a first intermediate bone block and a second intermediate bone block, and the tendon is secured between the first intermediate bone block and the second intermediate bone block of the first bone block assembly at the first end or at the first intermediate section of the tendon. Additionally, the second bone block assembly comprises at least a first intermediate bone block and a second intermediate bone block, and the tendon is secured between the first intermediate bone block and the second intermediate bone block of the second bone block assembly at the second end or at the second intermediate section of the tendon. Furthermore, at least one of the first bone block assembly or the second bone block assembly provides at least one level of compression to the tendon prior to implantation and at least one different level of compression to the tendon after implantation.

In at least another particularly preferred embodiment, the present technology provides an implant comprising a tendon having a length, wherein the tendon comprises along its length at least a first end, a first intermediate section, a central section, a second intermediate section, and a second end; at least a first bone component having a naturally occurring attachment to the first end of the tendon; and a bone block assembly comprising at least a first intermediate bone block and a second intermediate bone block. In such embodiments, the tendon is secured between the first intermediate bone block and the second intermediate bone block of the bone block assembly, and the bone block assembly provides a first grip on the tendon prior to implantation and a second grip on the tendon after implantation.

In at least another particularly preferred embodiment, the present technology provides an implant comprising a tendon having a length, and a bone block assembly comprising at least a first intermediate bone block comprising cancellous bone and a second intermediate bone block comprising cancellous bone, wherein the tendon is secured between the first intermediate bone block and the second intermediate bone block at a fixed location along its length; and wherein at least one of the first intermediate bone block or the second intermediate bone block has a first geometric configuration prior to implantation of the implant into a patient and a second geometric configuration after implantation of the implant into a patient.

In at least another particularly preferred embodiment, the present technology provides an assembled bone tendon bone implant comprising a tendon having a length and an effective diameter; and a bone block assembly fixed along the length of the tendon, the bone block assembly comprising at least a first intermediate bone block and a second intermediate bone block, wherein the tendon is between the first intermediate bone block and the second intermediate bone block, and the first intermediate bone block and the second intermediate bone block are connected by at least one pin comprising cortical bone; wherein the bone block assembly has an effective diameter of from about 9 mm to about 12 mm; wherein the effective diameter of the tendon is between about 80% and about 120% of the effective diameter of the bone block assembly; wherein the width of at least one of the first intermediate bone block or the second intermediate bone block is from about 8.5 mm to about 12 mm, the length of at least one of the first intermediate bone block or the second intermediate bone block is from about 15 mm to about 30 mm; and the height of at least one of the first intermediate bone block or the second intermediate bone block is from about 3 mm to about 5 mm.

In at least certain of the above mentioned embodiments, the invention provides an assembled bone-tendon-bone graft wherein at least one or more, preferably two or more, and more preferably all of the bone block components are pre-attached to the tendon and have a predetermined position along the length of the tendon prior to implantation. In some particularly preferred embodiments, the predetermined position along the length of the tendon or the pre-attached configuration or both are at least partially maintained, preferably substantially maintained, and more preferably completely maintained following implantation of the graft into a patient in need of a tendon reconstruction implant.

In another aspect, the present technology provides methods of making bone-tendon-bone grafts. For example, in at least one embodiment, the present technology provides a method of forming an implant comprising the steps of providing a portion of a calcaneus bone having a natural attachment to an Achilles' tendon, separating the portion of a calcaneus bone into at least two pieces, and separating the Achilles' tendon into at least two sections by tearing the tendon along its fiber direction. In such embodiments of the present technology, the natural attachment to the Achilles' tendon is maintained on each piece of calcaneus bone when the bone is separated into pieces, and each section of the Achilles' tendon maintains a natural attachment to one piece of calcaneus bone when the tendon is separated. Preferably, the Achilles' tendon has a free end opposite the natural attachment and a length of at least about 40 mm from the natural attachment to the free end.

In some embodiments, the method further comprises the step of securing a bone component to the free end of the tendon. In other embodiments, the method further comprises securing a bone block assembly to the free end of the tendon. The step of securing a bone block assembly to the free end of the tendon can comprise providing a first intermediate bone block and a second intermediate bone block, compressing the free end of the tendon between the first intermediate bone block and the second intermediate bone block, and securing the tendon between the first intermediate bone block and the second intermediate bone block with at least one pin comprising cortical bone.

BRIEF DESCRIPTION OF SEVERAL VIEWS OF THE DRAWINGS

The Figures, and the discussion thereof, provided in this disclosure relate to various embodiments of the present technology. It should be understood that the Figures are illustrative in nature, and that modifications can be made thereto without departing from the scope of the present invention.

FIG. 1A is a side view of the illustrated embodiment. FIG. 1B is a top view of the illustrated embodiment. FIG. 1C is a perspective view of the illustrated embodiment. FIG. 1D is an end view of the illustrated embodiment looking at the assembled bone block.

FIG. 2A is a side view of the illustrated embodiment. FIG. 2B is a top view of the illustrated embodiment. FIG. 2C is a perspective view of the illustrated embodiment. FIG. 2D is an end view of the illustrated embodiment looking at the assembled bone block.

FIG. 3A is a side view of the illustrated embodiment. FIG. 3B is a top view of the illustrated embodiment. FIG. 3C is a perspective view of the illustrated embodiment. FIG. 3D is an end view of the illustrated embodiment.

FIG. 4A is a side view of the illustrated embodiment. FIG. 4B is a top view of the illustrated embodiment. FIG. 4C is a perspective view of the illustrated embodiment. FIG. 4D is an end view of the illustrated embodiment.

FIG. 5A is a side view of the illustrated embodiment. FIG. 5B is a top view of the illustrated embodiment. FIG. 5C is a perspective view of the illustrated embodiment. FIG. 5D is an end view of the illustrated embodiment.

FIGS. 6A-6G are end views of various embodiments of intermediate bone blocks for use in assembled bone blocks of the present technology. FIG. 6A is an end view of one embodiment of an intermediate bone block having a semi-circular end profile. FIG. 6B is an end view of one embodiment of an intermediate bone block having an end profile that is a circular segment. FIG. 6C is an end view of one embodiment of an intermediate bone block having an end profile that is a gibbous circular segment. FIG. 6D is an end view of one embodiment of an intermediate bone block having an end profile that is half of a hexagon or a modified hexagon. FIG. 6E is an end view of one embodiment of an intermediate bone block having an end profile that is half of an octagon or a modified octagon. FIG. 6F is an end view of one embodiment of an intermediate bone block having an asymmetrical triangular end profile. FIG. 6G is an end view of one embodiment of an intermediate bone block having a rectangular end profile.

FIGS. 7A-7D are views of one embodiment of an intermediate bone block for use in an assembled bone block of the present technology, having channels in the tissue engaging surface. FIG. 7A is a side view of the illustrated embodiment. FIG. 7B is a direct view of the tissue engaging surface of the illustrated embodiment. FIG. 7C is a perspective view of the illustrated embodiment. FIG. 7D is an end view of the illustrated embodiment.

FIGS. 8A-8D are views of one embodiment of an intermediate bone block for use in an assembled bone block of the present technology, having channels in the tissue engaging surface and a notched groove in the top surface. FIG. 8A is a side view of the illustrated embodiment. FIG. 8B is a top view of the illustrated embodiment. FIG. 8C is a perspective view of the illustrated embodiment. FIG. 8D is an end view of the illustrated embodiment.

FIGS. 9A-9G are end views of various embodiments of intermediate bone blocks for use in assembled bone blocks of the present technology. FIG. 9A is an end view of one embodiment of an intermediate bone block having a semicircular end profile with a notched groove in the top surface thereof. FIG. 9B is an end view of one embodiment of an intermediate bone block having an end profile that is a circular segment with a notched groove in the top surface thereof. FIG. 9C is an end view of one embodiment of an intermediate bone block having an end profile that is a gibbous circular segment with a notched groove in the top surface thereof. FIG. 9D is an end view of one embodiment of an intermediate bone block having an end profile that is half of a hexagon or a modified hexagon with a notched groove in the top surface thereof. FIG. 9E is an end view of one embodiment of an intermediate bone block having an end profile that is half of an octagon or a modified octagon with a notched groove in the top surface thereof. FIG. 9F is an end view of one embodiment of an intermediate bone block having an asymmetrical triangular end profile with a notched groove in the top surface thereof. FIG. 9G is an end view of one embodiment of an intermediate bone block having a rectangular end profile with a notched groove in the top surface thereof.

FIGS. 10A-10E are end views of various embodiments of intermediate bone blocks for use in assembled bone blocks of the present technology, where each intermediate bone block has a notched groove or a truncated top surface. FIG. 10A is an end view of one embodiment of an intermediate bone block having a hexagonal or modified hexagonal profile without a notched groove or truncation therein. FIG. 10B is an end view of one embodiment of an intermediate bone block having a hexagonal or modified hexagonal profile, and a notched groove having a curved end profile in the top surface thereof. FIG. 10C is an end view of one embodiment of an intermediate bone block having a hexagonal or modified hexagonal profile, and a notched groove having a "V" shaped end profile in the top surface thereof. FIG. 10D is an end view of one embodiment of an intermediate bone block having a hexagonal or modified hexagonal profile, and a notched groove having a rectangular end profile in the top surface thereof. FIG. 10E is an end view of one embodiment of an intermediate bone block having a truncated hexagonal or truncated modified hexagonal profile.

FIGS. 11A-11D are views of one embodiment of a separated intermediate bone block of the present technology. FIG. 11A is a top view of this embodiment of a separated intermediate bone block of the present technology. FIG. 11B is a perspective view of this embodiment of a separated intermediate bone block of the present technology. FIG. 11C is an end view of this embodiment of a separated intermediate bone block of the present technology.

FIG. 12A is a perspective view of this embodiment in a bone tunnel (not shown). FIG. 12B is an end view of the embodiment within a bone tunnel (shown).

FIG. 13A is a side view of one end of an implant of the present technology, having an assembled bone block securing one end of a tendon therein, and an interference screw having been inserted into the bone tunnel (not shown) on top of the assembled bone block. FIG. 13B is a side view of the embodiment shown in FIG. 13A, illustrating the embodiment within a bone tunnel. FIG. 13C is a perspective view of the illustrated embodiment (bone tunnel not shown). FIG. 13D is an end view of the illustrated embodiment within a bone tunnel.

FIG. 14A illustrates one embodiment of bone blank recovery, wherein the bone blanks are taken substantially from the subchondral bone beneath a load bearing cartilaginous region of a long bone. FIG. 14B illustrates a second embodiment of bone blank recovery, wherein the bone blanks are recovered partly within the subchondral region of the bone and partly within the cortical shell at the outer edge of the bone.

FIG. 15A is an end view of one embodiment of an assembled bone-tendon graft of the present technology, showing the bone block assembly and the location of section A-A. FIG. 15B is a top view of one embodiment of an assembled bone-tendon graft of the present technology, showing the tendon emerging from one end of the bone block assembly. FIG. 15C is a perspective view of one embodiment of an assembled bone-tendon graft of the present technology, showing the mounting holes entering through the top surface. The cross section A-A of FIG. 15D illustrates several possible end conditions for a bone pin.

DETAILED DESCRIPTION OF THE INVENTION

Figure 1C:
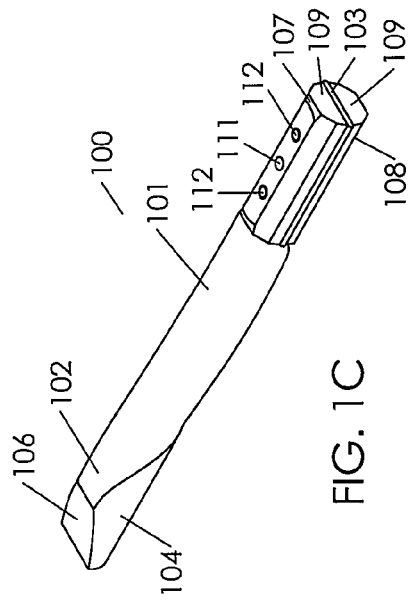
FIGS. 1A-1D are views of one embodiment of a bone-tendon-bone graft of the present technology having a tendon with a naturally occurring bone-tendon attachment at one end and an assembled bone block at the other end.

The present technology relates to bone-tendon and bone-tendon bone grafts or implants, also referred to herein as BTBs. More particularly, the present technology relates to assembled implants that comprise a length of tendon and at least two bone components or intermediate bone blocks that are assembled to form a BTB. Additionally, the present technology relates to methods of making such implants.

BTBs of the present technology generally comprise at least one bone block assembly. Accordingly, in some embodiments, the present technology provides an implant comprising a tendon having a length, wherein the tendon comprises along its length at least a first end, a first intermediate section, a central section, a second intermediate section, and a second end; and a bone block assembly comprising at least a first intermediate bone block and a second intermediate bone block; wherein the bone block assembly has a first grip on the tendon prior to implantation of the implant into a patient and a second grip on the tendon after implantation of the implant into a patient. In preferred embodiments, the tendon is secured between the first intermediate bone block and the second intermediate bone block at a fixed location along its length at the first end or at the first intermediate section of the tendon.

In some embodiments, the tendon has a natural attachment to a bone component at the end of the implant opposite the bone block assembly. In some other embodiments, there is a second bone block assembly at the end of the implant opposite the first bone block assembly.

Various embodiments of the present technology can provide advantages over BTBs currently used in orthopedic medicine. For example, at least some embodiments of the present invention preferably provide an implant having high tensile strength, such as is desirable for ACL repairs, wherein the implant also has reduced slippage and/or tearing such as is recognized in the orthopedic field in association with some currently used practices as described above. As another example, at least some embodiments of the present invention preferably provide a BTB having a robust design, simple components, ease of manufacturability, and/or high reliability, all while maintaining an acceptable tensile strength, stiffness, and elongation performance. These aspects of BTBs are especially preferred for embodiments that are to be implanted in athletes and other individuals where maximum performance is required. It is also preferred in at least some embodiments of the present technology that the implants provided have a predetermined set of design parameters including gauge length, tendon size, implant effective diameter, bone component dimensions, and implant component orientation. It is further preferred that at least some embodiments of the present invention are configured and adapted to be readily sterilized by a non-damaging tissue sterilization process such as that disclosed in applicants' issued U.S. Pat. No. 6,482,584 and related applications, issued and pending. To be readily sterilized by such a process, a tissue implant should be free of occlusive spaces, trapped interior spaces or chambers, tightly bound soft tissues or tendons, and design features which would restrict the perfusion of sterilants into and out of the interior of the tissue.

Figure 14B:
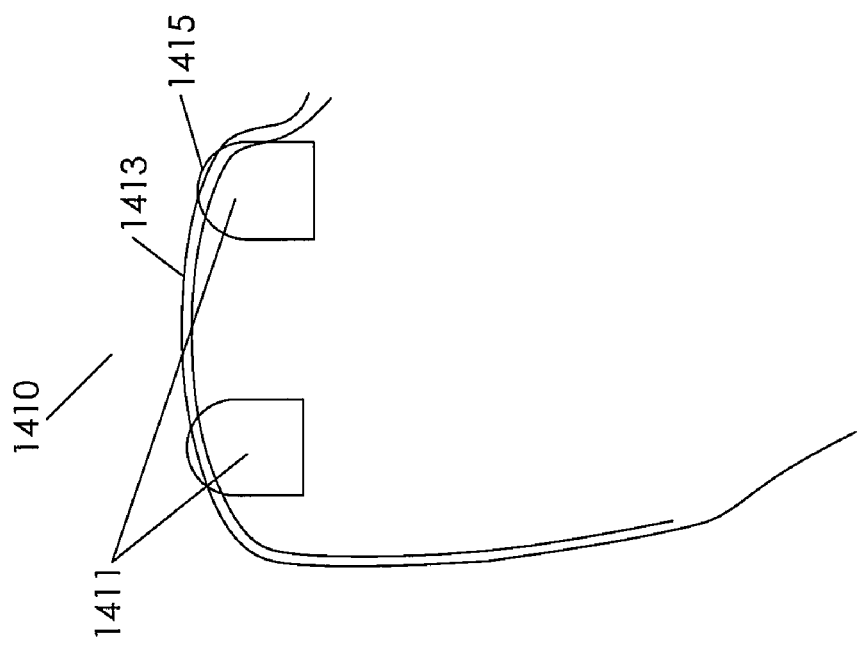
FIGS. 14A-14B are side views of a long bone, from which bone blanks for use in making bone components of the present technology can be recovered.
Figure 14A:
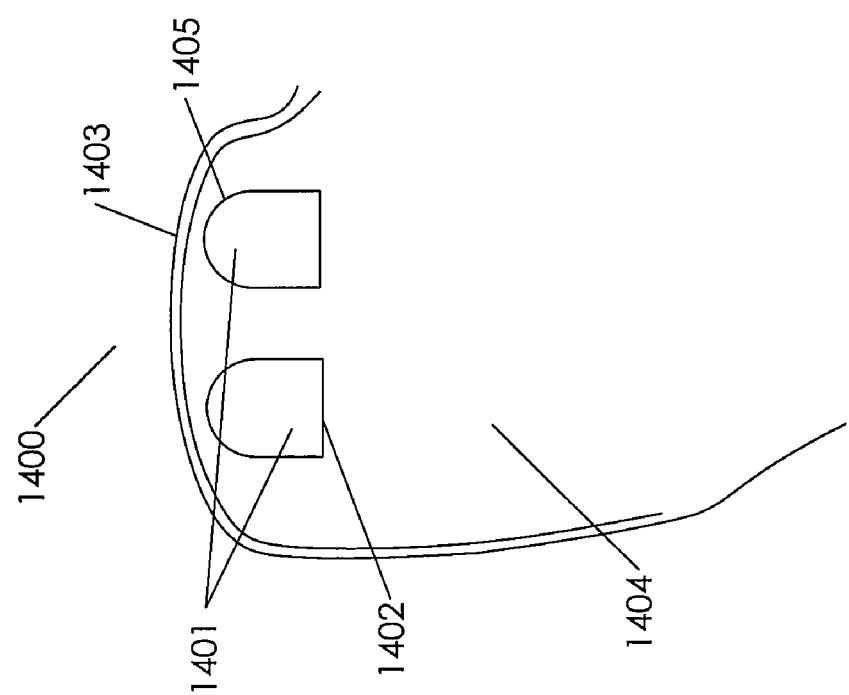

Furthermore, another advantage provided by some embodiments of the present technology is an increase in the quantity of implants utilizing non-synthetic materials, particularly in embodiments of the present technology comprising allograft or xenograft bone. As discussed above, when a BTB is cut as a single piece from a section of the patella (bone), patellar tendon and the tibia (bone) of the donor, a maximum of only 2-3 grafts can generally be obtained per knee of the donor. Some embodiments of the present technology permit a greater number of implants to be made from materials recovered from a single donor. For example, particularly preferred embodiments of the present technology utilize tendons other than the patellar tendon, such as the Achilles' tendon. Additionally, bone components, particularly bone utilized in making intermediate bone blocks of the present technology are preferably recovered from subchondral bone, more preferably from areas near load bearing cartilaginous regions of long bones. These regions are typically under utilized due to their location, complex topology, and transition from cortical to dense cancellous bone in a very small area bounded by the curved exterior of the end of the long bone. Recovering bone components from these areas utilizes bone that has not previously been commonly utilized in BTBs and that has been underutilized in the creation of other allograft and xenograft implants, and thus increases the number of bone components that can be derived from a single donor. As illustrated in FIGS. 14A and B, the subchondral bone often comes from just beneath a convex cortical cap. Due to the small height of the intermediate bone blocks of the present invention, this bone can be utilized here, where the curvature and transition into the cortical cap would make the same material less desirable for common uses of cancellous bone such as assembled spinal implants which typically require large rectangular blocks of cancellous bone. The subchondral bone is typically recovered from just under the cortical cap, up to about 10 mm below the cortical bone, alternatively up to about 15 mm below the cortical bone, alternatively up to about 20 mm below the cortical bone. The subchondral bone may also be recovered with at least a portion of the cortical material still attached. The cortical material may be maintained, modified, or removed during processing. It should be understood that cancellous bone properties vary at different locations in the same donor bone, vary more so among different donors, and may vary even more widely across allograft and xenograft tissues. Variations in the properties of cancellous bone material are expected across different species of (including human) donors, across age ranges within a population of donors, and across genetic and demographic population groups within a population of donors. Making advantageous use of the particular combination of properties found at a given donor cancellous bone location is contemplated by and is an object of the present invention.

It has been surprisingly discovered that various design parameters and manufacturing methods of the present technology can result in BTB implants of the present technology having improved strength as compared to certain other implants. For example, implants that grip a tendon utilizing a bone block assembly can have improved performance when they are designed and configured such that the nature of the grip on the tendon changes from its pre-implantation state to its post-implantation state, while the general location and orientation of the bone block assemblies relative to the tendon is maintained preferably at exactly the same, or alternatively at about the same position in at least one dimension. As another example, it has been found that the strength of non-synthetic (natural) tendon materials utilized in BTBs can be improved when they are recovered from a whole tendon, as it exists in the human body, and prepared in a manner that separates the whole tendon into sections along the fiber direction rather than trimming or cutting through or across fibers within the tendon. Accordingly, at least some embodiments, as discussed below, incorporate these findings into the design and preparation of BTBs of the present technology.

Furthermore, in at least some preferred embodiments, a BTB implant of the present technology has a stiffness of at least about 90N/mm, preferably at least about 150N/mm. The minimum limit of 90N/mm is derived from a combination of the published requirement of about 450N load to withstand the activities of daily living (Noyes, 1984), and the accepted industry standard of 5 mm maximum differential laxity in a reconstructed knee (IKDC subjective knee evaluation form, 2006). Additionally, in at least some preferred embodiments, a BTB implant of the present technology has an elongation of about 5 mm or less than about 5 mm, preferably less than about 2 mm, and more preferably less than about 1 mm. Stiffness and elongation for any given BTB implant can be calculated by methods known in the art. Stiffness is defined as the slope of the force-displacement curve when the implant is subject to axial load increasing from below 100 Newtons to above at least 200 Newtons. Elongation is defined as the difference in length for an implant measured before the first cycle of a dynamic load test and after 1000 cycles of loading to at least 200 Newtons. Factors such as a shorter gauge length and a larger tendon both tend to improve stiffness. Additionally, certain tendons within human or xenograft anatomy are known in the art to have higher or lower inherent stiffness in the tendon material itself. For example, in the human anatomy a peroneus tendon is known to be of good stiffness, while the adductor tendon is known to have less stiffness.

In some embodiments of the present technology, an implant is provided that comprises a tendon and a bone block assembly, where the bone block assembly comprises at least a first intermediate bone block and a second intermediate bone block. Bone block assemblies of the present technology generally comprise at least two intermediate bone blocks, and can comprise three, four, five, or more than five intermediate bone blocks. Bone block assemblies of the present technology can be formed by placing the intermediate bone blocks in close abutment or in spaced positions relative to one another, and using at least one biocompatible connector to attach or secure them to one another. In some preferred embodiments of the present technology, intermediate bone blocks have holes therein which are aligned when the intermediate bone blocks are in a desired position relative to one another, and the at least one biocompatible connector can be inserted through the aligned holes to attach or secure the intermediate bone blocks. In particularly preferred embodiments, the tendon is sandwiched between at least two intermediate bone blocks and at least one biocompatible connector is inserted through the tendon between the first intermediate bone block and the second intermediate bone block, to secure the tendon therebetween.

Biocompatible connectors suitable for use with the present technology include any biocompatible connectors capable of holding the bone intermediate bone blocks together as a unit (i.e., an assembled bone block). Some examples of biocompatible connectors include rigid pins and flexible connectors. Some examples of rigid pins include pins comprising stainless steel, titanium, or cortical bone. Particularly preferred rigid pins are cortical bone pins (i.e., pins made from cortical bone). One manner by which rigid pins can hold intermediate bone blocks together as a unit is by forming an interference fit with the holes of the intermediate bone blocks into which they are inserted. Some examples of flexible connectors include connectors comprising collagenous material, suture, biocompatible polymers, bioabsorbale polymers, bioabsorbable polymers, or bioresorbable polymers.

In particularly preferred embodiments, a bone block assembly provides a first grip on the tendon prior to implantation of the implant into a patient and a second grip on the tendon after implantation of the implant into a patient. The grip that a bone block assembly, or a bone component such as an intermediate bone block that is par of a bone block assembly, has on a tendon can also be referred to, for example, as the hold, fix, clamp, grab, or bite. For example, without wanting to be bound by any particular theory, it is believed that certain gripping channels, such as omega channel configurations previously disclosed by the applicants in co-pending U.S. Patent Application Publication Nos. 20060229722; 20060200236; 20060200235; and 20060212036 provide a mechanism to grab or hold individual tendon fibers or bundles of tendon fibers within an intermediate bone block or bone block assembly. Although omega channel configurations have been shown to have superior holding ability over other similar channel configurations, it is believed that either omega channel configurations or other channel configurations may be configured and adapted to provide a sufficient gripping surface when used with the other elements of the present invention. Additionally, it is believed that the natural texture of a cross section of regular cancellous bone or of dense or subchondral cancellous bone provides a similar mechanism working on a smaller scale to grab or hold the tendon at the surface by a process hypothesized to include micro-infusion of tendon material into the surface pores or openings of the cancellous matrix. It is further believed that a cross section of dense or subchondral cancellous bone may provide a superior gripping surface as compared to a cross section of regular cancellous or cortical bone; but that a cross section regular cancellous bone may also provide a sufficient grip for some applications. Furthermore, it is also believed that cortical or cancellous intermediate bone blocks configured to break, crush down, or shift in at least one direction upon insertion or fixation of the graft in a patient can provide a first and second grip or improved bite on the tendon.

The term "grip" is used broadly herein to encompass any manner in which the intermediate bone blocks of a bone block assembly contact a tendon and exert force on the tendon or otherwise provide resistance to tendon slippage. Forces exerted upon a tendon by an intermediate bone block or a bone block assembly of the present technology can include, but are not limited to, compressive, frictional, tensional, and rotational forces. For example, in some preferred embodiments, the first grip of the bone block assembly on the tendon provides one level of compression to the tendon prior to implantation of the implant into a patient, and the second grip provides a second level of compression to the tendon after implantation of the implant into a patient.

As discussed in more detail below, the grip of a bone block assembly on a tendon can be altered in various ways. One preferred manner is to have at least one intermediate bone block in a bone block assembly that has a first geometric configuration prior to implantation of the implant, and a second geometric configuration after implantation of the implant. Also, as discussed in more detail below, intermediate bone blocks of the present technology can comprise a tendon engaging surface that has a texture. In at least some embodiments, such textured surfaces can grip and hold tendon to resist tendon slippage, particularly when utilized in conjunction with forces such as compressive forces within a bone block assembly.

Tendons

Tendons of the present technology have a length that can be described conceptually as having several portions or sections along the length of the tendon. For example, a tendon of the present technology can be described comprising along its length at least a first end, a first intermediate section, a central section, a second intermediate section, and a second end. These sections can be conceptualized, for example, as transitioning from one section to the next starting at one end of the tendon and traversing the length of the tendon. The length of the first or second end, for example, can be from about the tip of the tendon up to about 30 mm along the length of the tendon. The length of the first or second intermediate section can be from about 5 mm along the length of the tendon, as measured from either tip, to about 50 mm along the length of the tendon. The central section of the tendon includes the midpoint of the tendon and any area along the length of the tendon on either side of the midpoint that is not otherwise covered by one of the other sections.

In at least some preferred embodiments of the present technology, the tendon is secured by a bone block assembly, such as being secured between a first intermediate bone block and a second intermediate bone block, at a fixed location along its length at the first end or at the first intermediate section of the tendon. For example, when the tendon is secured between the first intermediate bone block and the second intermediate bone block at the first intermediate section of the tendon, the first end of the tendon can form a tendon tail that extends beyond the first intermediate bone block and the second intermediate bone block. The tendon tail can be useful for surgical placement and/or fixation. Tendon tails can be any length suitable for the intended end use thereof, but are typically from about 1 mm to about 20 mm in length, preferably from about 2 to about 10 mm in length, and more preferably about 5 mm in length. A tendon tail may serve as a point of connection for clamps, forceps or other means of gripping a tendon during surgery or in graft preparation. Suture is typically passed through the tendon tail to provide a means of pulling the graft up through the surgical tunnels and to provide a means of applying tension to the graft during insertion and during fixation. A tail is typically provided at each end of the graft, but may be provided at one end, or both ends, or neither. When a tail is provided at both ends of the graft, the tails are typically the same, but may also be of different length, width, or thickness.

As discussed above, the term "tendon," as used generally herein to refer to the "tendon" (soft tissue) portion of a BTB of the present technology, means a length of tendon, a bundle of tendons of the same or different lengths, a length of ligament, a bundle of ligaments of the same length or different lengths, a segment or segments of pericardium, dermis or fascia, dura, skin, submucosal tissue (e.g., intestinal tissue), cartilage, other natural materials, synthetic materials, or a combination thereof. When "tendons" are formed from bundled tissues, the tissues can be of the same thickness or of different thicknesses. Bundled tissues utilized in the tendon portion of a BTB of the present technology can also be of the same cross-sectional area or of different cross-sectional areas.

In some situations, particularly in tendon repair, a tendon bundle comprising a xenograft tendon bundle or a combination of allograft and xenograft tendons of different thicknesses and lengths, can provide for enhanced performance under extreme stresses. As used herein, the term "bundle" refers to 1-10 discrete segments such as tendons or ligaments, which themselves can be made up of smaller fibers that are stapled, glued, sutured, woven or braided. Alternatively, segments made of tendons or other soft tissues can be crosslinked with a crosslinking agent. By selecting a bundle of tendons or ligaments of different length, or a combination thereof, an assembled BTB of the present invention can be tailored to the needs of the patient.

It is also contemplated that the tendon portion of a BTB implant of the present technology can be an engineered construct of natural or synthetic origin, such as a synthetic ligament repair scaffold, other flexible synthetic biomaterial, or specially formulated natural material such as that disclosed in the applicant's copending applications U.S. patent application Ser. No. 10/754,310, entitled "Matrix Composition For Human Grafts/Implants" and filed Jan. 9, 2004, and in U.S. patent application Ser. No. 10/793,976, entitled "Muscle-Based Grafts/Implants" and filed Mar. 5, 2004. Engineered constructs include, but are not limited to, processed collagen-based tissue matrix, such as the product sold under the trade name GraftJacket®, by Wright Medical Technology, Inc., Arlington, Tenn.

When natural materials are used as the tendon (soft tissue) portion of a BTB implant, the material is typically autograft, allograft or xenograft. Preferably, the source of the tendon is allograft or xenograft. When the recipient patient is a human, the source is preferably human allograft. In at least some preferred embodiments, a BTB of the present technology can be formed using an Achilles' tendon. Allograft Achilles' tendons are particularly preferred in some embodiments, including, for example, BTBs having a naturally occurring bone block-tendon attachment at one end thereof. Other natural soft tissue materials that can be used as the tendon portion of a BTB implant of the present technology include, but are not limited to patellar tendons, gracilis, semitendonosis, anterior tibialis, posterior tibialis, peroneus longus, peroneus brevis, quadriceps, adductor, abductor, hallucis longus, sartorius. Viable natural attachments to bone blocks can be utilized in some embodiments of the present technology with patellar, quadriceps and Achilles' tendons. Ultimately, each tendon used with the present technology should be selected on the basis of having a desired combination of tendon size, strength and stiffness. Certain tendons, such as satorius, or the abductor/adductor tendons may be undesirable for certain embodiments due to excessive stretch and potential for laxity, unless design changes are made to compensate for these properties. Other tendons, such as gracilis and semitendonosis may be undesirable because of their small size. Smaller tendons may be too weak use in certain embodiments, or, even if strong enough for a given application, surgeon preference or distrust may make them undesirable. Doubling, or even quadrupling strands of smaller tendons is well known in the art as one way to overcome tendon strength concerns which might be reapplied to assembled grafts of the present technology.

One method of making an implant of the present technology having a natural bone-tendon attachment at one end thereof includes deriving the tendon portion and the naturally attached bone component portion from a whole tendon and a portion of bone that is naturally attached to the whole tendon. A whole tendon is a length of tendon, whether being the entire length or less than the entire length, as recovered from a donor. The lengthwise direction of a whole tendon can also be referred to as the tendon's major direction. Tendons generally have fiber bundles running in a fiber direction along the major direction of the tendon. The fiber direction can differ from the tendon major direction over at least a portion of the tendon length. A whole tendon may be advantageously processed into smaller sections along its length by separating the natural fiber bundles, thus creating one or more smaller tendon sections while maximizing the available tendon strength from the remaining intact bundles.

For example, one aspect the present technology makes use of subtle anatomical features found inside some tendons, such as the Achilles' tendon. The Achilles' tendon is an example of a tendon with a natural double-bundle internal structure. This structure often goes unnoticed or unappreciated, and has not been a broad topic of study in the art, but was discovered by the applicants to have advantageous elements. The Achilles' tendon attaches distally to the calcaneal bone block, and proximally to the two heads of the gastrocnemius and soleus muscles. Most textbooks and references focus on the musculature and bones, treating tendons as monolithic extensions or endpoints of the muscles they connect, and so it was only upon close inspection and analysis of the Achilles tendon and calcaneal bone block that the applicants discovered the unique and advantageous features of the double bundle anatomy.

The fiber bundles of the Achilles tendon intertwine, twist and rotate around each other between their natural attachment at the calcaneal bone and their endpoints in the gastrocnemius and soleus muscles. Traditional techniques known in the art for recovering components of a BTB implant that include a natural attachment to the Achilles' tendon include coring (with a hollow coring drill) a section of the calcaneal bone block to make a bone tendon graft, trimming away excess tendon without regard to fiber orientation, then either attaching a single piece of bone or other fixation element to the remaining free end of the tendon by suture or some other means, or utilizing a soft tissue fixation technique also known in the art to fix the free tendon in the bone tunnel. Cutting or trimming the tendon without regard for the fiber direction often results in cutting across fibers or fiber bundles and thereby weakening the tendon. In contrast, with the present technology, it has been surprisingly discovered that a stronger, more cohesive and more uniform bone-tendon segment can be obtained by splitting the calcaneal bone block near the separation of the two tendon bundles, carefully locating a starting point near the natural attachment of tendon to bone, then separating the tendon along the fiber bundles an in the fiber direction. When combined with an assembled bone block of the present technology, a strong, reliable, readily available new allograft construct can be created.

Therefore, in at least one method of the present technology, an initial step is providing a portion of a calcaneus bone having a natural attachment to an Achilles' tendon. The Achilles' tendon preferably has a free end opposite the natural attachment and a length of at least about 40 mm from the natural attachment to the free end. Another step is preferably separating the portion of a calcaneus bone into at least two pieces, wherein the natural attachment to the Achilles' tendon is maintained on each piece of calcaneus bone. After the portion of calcaneus bone is separated, another step is separating the Achilles' tendon into at least two sections by separating or tearing the tendon along its fiber direction, wherein each section of the Achilles' tendon maintains a natural attachment to one piece of calcaneus bone. Separating the bone prior to separating the tendon is a preferred method because it may not always possible to see or predict exactly where the tendon bundle might separate from the free end down to the bone block. By separating the bone block first, and then separating the tendon from there, graft size, utilization of tissue, graft strength, and graft geometry are more easily optimized. Separating the bone block, e.g., by cutting, chiseling, or breaking, is preferred over coring with a hollow rotary coring bit. Separating the bone block can allow for more precise control and placement of the cut relative to tendon fibers, and for less chance of damage to tendon fibers. Separating the bone block and then separating or tearing the tendon along the fiber direction is preferred to traditional trimming, de-bulking, or cutting of the tendon because the separation process maintains more of the tendon fibers in continuity along the length of the tendon bundle and is less likely to cut through or damage any fibers or fiber bundles, resulting in greater strength for the finished implant.

Furthermore, in at least one preferred embodiment of the present technology having a naturally occurring bone-tendon attachment at one end thereof, an implant is provided wherein the tendon is derived from a section of a whole tendon, wherein the whole tendon has a major direction along its length and the whole tendon comprises fiber bundles oriented in a fiber direction, wherein the fiber direction differs from the major direction of the whole tendon over at least a portion of the length of the whole tendon; and wherein the whole tendon is separated into sections along the fiber direction.

Desirable lengths for tendons of the present technology depend upon the application and the size of the patient. The gauge length of implants of the present technology can be from about 30 mm to about 55 mm. The gauge length of an implant is the shortest distance between the bone components along the length of the tendon. Preferably, the gauge length of implants of the present technology is from about 38 mm to about 50 mm, more preferably, from about 40 mm to about 48 mm, and most preferably from about 42 mm to about 46 mm. The tendon length can be equal to, or greater than the gauge length of the implant. In the case of a BTB implant intended for anterior cruciate ligament repair or reconstruction in a human patient, the length of the tendon can be from about 32 mm to about 58 mm, preferably from about 38 mm to about 52 mm, and more preferably from about 42 mm to about 48 mm.

BTB Implants Having a Naturally Occurring Bone-Tendon Attachment

In some preferred embodiments of the present technology, a bone-tendon-bone implant is provided that has a naturally occurring bone-tendon attachment on one end thereof. Accordingly, a BTB of the present technology can comprise at least a first bone component at the second end of the implant, wherein the first bone component has a naturally occurring attachment to the second end of the tendon. In at least one preferred embodiment of this type, an implant is provided that comprises a tendon having a length, wherein the tendon comprises along its length at least a first end, a first intermediate section, a central section, a second intermediate section, and a second end; at least a first bone component having a naturally occurring attachment to the first end of the tendon; a bone block assembly comprising at least a first intermediate bone block and a second intermediate bone block; wherein the tendon is secured between the first intermediate bone block and the second intermediate bone block of the bone block assembly; and wherein the bone block assembly provides a first grip on the tendon prior to implantation and a second grip on the tendon after implantation.

Figure 1D:
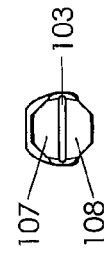
Figure 1B:
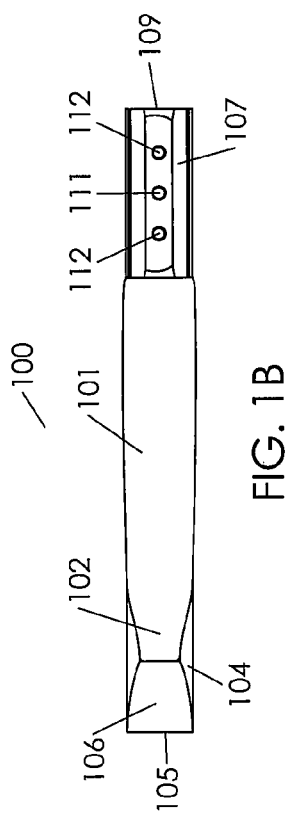
Figure 1A:
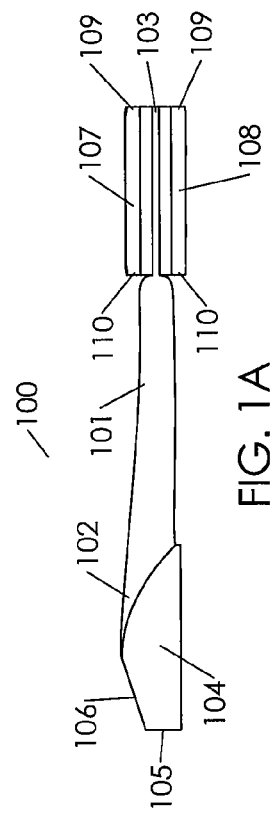

For example, FIGS. 1A to 1D are views of one embodiment of a bone-tendon-bone graft of the present technology having a tendon with a naturally occurring bone tendon attachment at one end and an assembled bone block at the other end. FIG. 1A is a side view of the implant 100. Tendon 101 as illustrated in FIG. 1A comprises a first end 103 and a second end that has naturally occurring attachment 102 to bone component 104. As illustrated, first end 103 of tendon 101 is secured between first intermediate bone block 107 and second intermediate bone block 108, which form a bone block assembly. Intermediate bone blocks 107 and 108 each have a distal end 109 and a proximal end 110. The distal end of any bone component in an implant of the present technology is the end farthest from the center of the tendon. As illustrated, first end 103 of tendon 101 is secured between first intermediate bone block 107 and second intermediate bone block 108 with no amount of tendon overhanging or extending beyond any of the edges of the intermediate bone blocks. It should be understood that the tendon would still be considered to the secured between first intermediate bone block 107 and second intermediate bone block 108 at first end 103 even if there was some amount of tendon overhanging or extending past the side edges or end of the intermediate bone blocks. Generally, a tendon can be considered to be secured within a bone block assembly at an "end" of the tendon when there is from about 0 mm to about 3 mm of tendon extending beyond the distal end 109 of the bone block assembly. Additionally, a tendon can be considered to be secured within a bone block assembly at an "intermediate section" when there is from about greater than about 3 mm of tendon extending beyond the distal end 109 of the bone block assembly. Any amount of tendon extending beyond the intermediate bone blocks of the bone block assembly is generally referred to as being a tendon tail.

As further illustrated in FIG. 1A, bone component 104 has a distal end 105 and a naturally occurring attachment 102 to tendon 101. Bone component 104 as illustrated also has a tapered top surface 106 such that the highest point of bone component 104 is located at naturally occurring attachment 102 and the top surface 106 of bone component 104 tapers down to front end 105.

FIG. 1B is a top view of implant 100, and further illustrates bone component 104 having front end 105 and tapered top surface 106 as well as naturally occurring attachment 102 to tendon 101. As shown in the top view of FIG. 1B, intermediate bone block 107 has three through-holes. Through-holes extend from the top surface of a bone component of the present technology to the bottom surface thereof. When a bone component of the present technology is an intermediate bone block, the bottom surface can also be referred to as the tissue engaging surface. Preferred embodiments of intermediate bone blocks of the present technology have at least one through-hole, and preferably at least two through-holes. Intermediate bone blocks of the present technology can have greater than two through-holes, such as having three, four, five, or more through-holes. It is preferred that when intermediate bone block 107 has three through-holes, that intermediate bone block 108 also have three through-holes, and that the holes in each of intermediate bone blocks 107 and 108 are in alignment when the intermediate bone blocks are assembled to form a bone block assembly.

Of the three holes illustrated in intermediate bone block 107 of FIG. 1B, hole 111 is preferably a graft manipulation hole by which the graft can be maneuvered. One manner in which the graft can be maneuvered is to insert suture through the implant at hole 111 and to use the suture to pull the implant in any desired direction. Due, at least in part, to this method of maneuvering the implant, hole 111 can also be referred to as being a suture hole. Holes 112 are preferably holes through which pin comprising cortical bone can be inserted to secure the assembled bone block and the tendon that is held between the intermediate bone blocks of the bone block assembly.

FIG. 1C is a perspective view of implant 100, and shows bone component 104 having tapered top surface 106 and naturally occurring attachment 102 to tendon 101. FIG. 1C also illustrates first end 103 of tendon 101 secured between intermediate bone block 107 and intermediate bone block 108. FIG. 1C further illustrates intermediate bone block 107 having graft manipulation hole 111 and two holes 112 through which biocompatible connectors can be inserted to secure the bone block assembly.

FIG. 1D is an end view of the bone block assembly of implant 100, comprising intermediate bone block 107 and intermediate bone block 108 with first end 103 of the tendon sandwiched and secured therebetween.

In particularly preferred embodiments of implants having a naturally occurring bone-tendon attachment, the bone component 104 having the natural attachment to the tendon is derived from an allograft or xenograft calcaneus bone and the tendon is derived from an Achilles' tendon naturally attached to the calcaneus bone. Bone component 104 preferably comprises primarily cancellous bone, although a thin cortical shell or cap can be located on the top portion of bone component 104 at the naturally occurring attachment to the tendon.

When embodiments of the present technology comprising a naturally occurring attachment between a bone component and a tendon are used in ACL reconstruction, the bone component having the naturally occurring attachment to the tendon is preferably the femoral side of the implant. In such embodiments, bone component 104 should be of a size and shape that it will easily slide through the femoral tunnel. The end 103 of the tendon, secured within a bone block assembly comprising at least a first intermediate bone block and a second intermediate bone block, is preferably the tibial side of the implant. The overall size and shape of the bone block assembly and the tendon secured therein should therefore allow for the bone block assembly to easily slide through the tibial tunnel. Femoral and tibial tunnels can vary in diameter from patient to patient, but are generally from about 9 mm to about 12 mm in diameter, although the bone tunnel is sometimes up to about 14 mm in diameter, and may be as much as 18-20 mm in diameter, particularly in instances of revision operations. The functional upper limit for tunnel size is ultimately determined by the size of the available bone bed in the patient's bone, e.g., the size of the femur and tibia in an ACL replacement procedure. The desired surgical tunnel sizes require a nominal bone block assembly effective diameter typically between about 8 mm to about 20 mm, alternatively between about 9 mm and about 14 mm, preferably between about 9 mm and about 12 mm, and more preferably between about 9 mm and about 11 mm. The tendon typically has an effective diameter between about 50% to about 150% of the effective diameter of the bone block assembly, preferably between about 70% to about 130% of the effective diameter of the bone block assembly, more preferably between about 80% to about 120% of the effective diameter of the bone block assembly, and even more preferably between about 95% to about 110% of the effective diameter of the bone block assembly. The effective diameter of the tendon is the widest measurement of the tendon, which limits the size of the tunnel through which the tendon will fit. It should be understood that tendons can often fold or compress somewhat during manipulation and insertion, and that the effective diameter can be affected by this phenomenon.

The preferred insertion direction for embodiments of implants having a naturally occurring bone-tendon attachment is to insert the implant with the bone block having the natural tendon attachment as the leading bone block. One benefit of this graft insertion orientation is that the naturally occurring attachment and bone block will readily accept any fixation technique preferred by the surgeon, as most fixation techniques or fixation apparatus are developed with natural bone blocks in mind. Thus, the surgeon is free to use either an interference screw, a cross pin, or an endo button as primary fixation, often backed up by a secondary fixation in the upper (femoral) tunnel. The surgeon can then select an interference screw for fixation in the lower (tibial) tunnel, either with or without secondary fixation. Alternatively, the surgeon may elect to fix the assembled end in the femoral tunnel to maximize compression and second grip force due to more dense bone material typically found in the femur as compared to the tibia During implantation of embodiments of the present technology having a naturally occurring bone-tendon attachment, fixation methods suitable for securing the bone block with the natural tendon attachment include, but are not limited to, staples, buttons, screw and washer, interference screws, and self-taping screws. In a preferred embodiment, fixation is accomplished by one or more interference screws, self-taping screws, or a combination thereof. Fixation methods for securing bone block assemblies in a human patient are discussed below. It is generally preferred to have at least one graft manipulation hole or tendon tail present on the femoral bone block or bone block assembly, to allow for pulling the graft up through the tunnels and manipulating the graft prior to fixation. Since the tibia is typically fixed following the femur, it is preferred to have at least two sutures and preferably two suture holes or graft manipulation holes in the tibial bone block to allow for additional redundant loops of suture which can be used to apply a higher tension to the graft when fixing the second (tibial) end. It has also been observed that a second or additional loop of suture material is more resistant to failure during insertion of an interference screw. Suture holes may be cut into an assembled bone block, or drilled through a naturally attached bone block.

FIGS. 2A-2D illustrate another embodiment of a bone-tendon-bone graft of the present technology having a naturally occurring attachment between a bone component at one end of the implant and the tendon portion of the implant. In this embodiment, the implant further comprises a second bone component secured to the first bone component. The second bone component preferably comprises cancellous bone or cortical bone. The second bone component also preferably comprises allograft or xenograft bone.

Figure 2C:
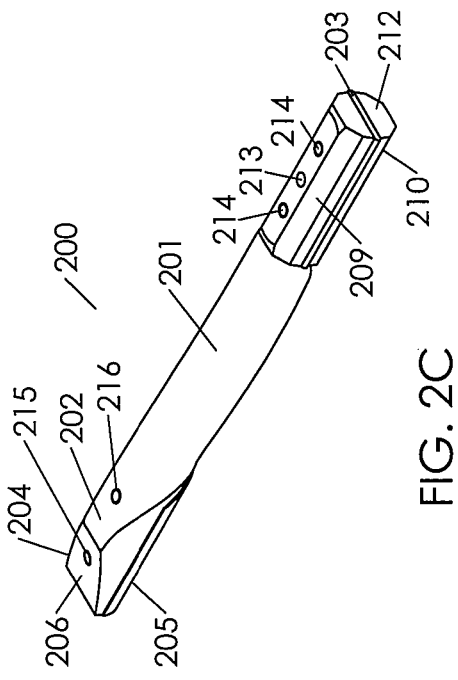
FIGS. 2A-2D are views of one embodiment of a bone-tendon-bone graft of the present technology having a tendon with a naturally occurring bone-tendon attachment and an additional bone component at one end, and an assembled bone block at the other end.
Figure 2D:
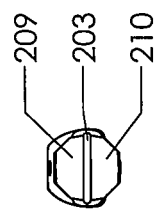
Figure 2B:
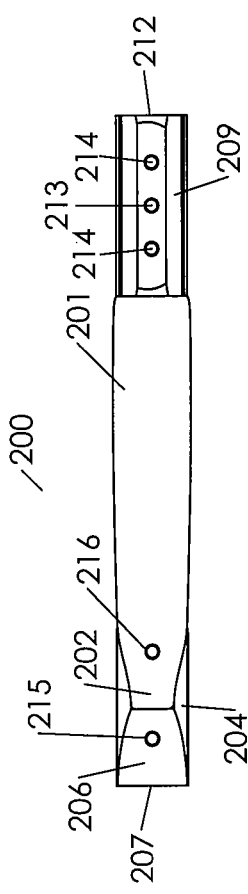
Figure 2A:
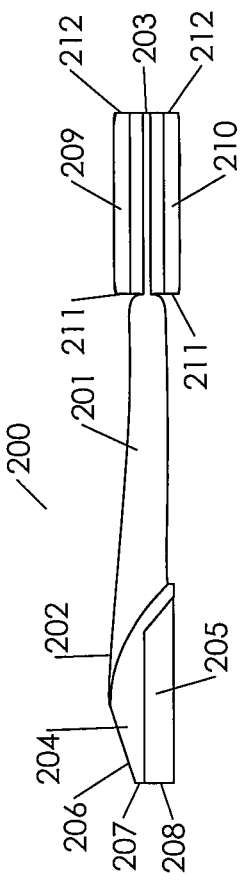

FIG. 2A is a side view of implant 200 which comprises tendon 201 having naturally occurring attachment 202 to bone component 204 as illustrated in FIG. 2A, the first end 203 of tendon 201 is secured between intermediate bone block 209 and intermediate bone block 210. Intermediate bone blocks 209 and 210 each have a distal end 212 and a proximal end 211. As illustrated in FIG. 2A, bone component 204 has a tapered top surface 206 and a distal end 207. A second bone component 205 is secured to bone component 204. Second bone component 205 has distal end 208.

FIG. 2B is a top view of implant 200, illustrating tendon 201 that has a naturally occurring attachment 202 to bone component 204. In preferred embodiments of the present technology where at least a second bone component 205 is secured to the first bone component 204, the first bone component 204 preferably has at least one through-hole, and can have two, three, four, five, or greater than five through-holes. The top view of implant 200 shown in FIG. 2B illustrates two through-holes 215 and 216 in bone component 204.

In some preferred embodiments, the second bone component is secured to the first bone component by at least one biocompatible connector. In such preferred embodiments, second bone component 205 preferably has at least one through-hole that is in alignment with at least one through-hole in first bone component 204 when the two bone components are in juxtaposition for assembly. Bone components 204 and 205 can be secured to one another by inserting at least one biocompatible connector into the aligned holes, that are preferably through-holes. In some particularly preferred embodiments, first bone component 204 and second bone component 205 each have at least two through-holes that are in alignment when the bone components are in juxtaposition for assembly to form two sets of aligned through-holes, and at least one set of aligned through holes forms a graft manipulation hole.

As further illustrated in FIG. 2B, intermediate bone block 209 has three through-holes. In preferred embodiments, hole 213 is a graft manipulation hole and holes 214 each have a biocompatible connector inserted therein to secure the bone block assembly.

FIG. 2C is a perspective view of implant 200 showing tendon 201 having naturally occurring attachment 202 to bone portion 204 and first end 203 secured by a bone block assembly comprising intermediate bone block 209 and intermediate bone block 210.

FIG. 2D is an end view illustrating the bone block assembly of implant 200 comprising intermediate bone block 209 and intermediate bone block 210 with the first end 203 of the tendon secured therebetween.

BTB Implants Having a Assembled Bone Blocks at Each End

Some preferred embodiments of the present technology provide a BTB implant comprising a tendon, a first bone block assembly and a second bone block assembly. The tendon and each of the bone block assemblies are preferably derived from allograft materials originating from a single donor, xenograft materials originating from a single donor, or from a biocompatible synthetic material. Furthermore, each intermediate bone block preferably comprises cancellous bone, cortical bone, both cancellous and cortical bone, or a biocompatible synthetic bone material. The second bone block assembly preferably comprises at least two intermediate bone blocks, and can comprise three, four, five or more than five intermediate bone blocks. The second bone block assembly can be of the same design and configuration as the first bone block assembly, or can be different in its design or configuration.

Some particularly preferred BTB implants of the present technology comprise a second bone block assembly, wherein the second bone block assembly comprises at least a first intermediate bone block and a second intermediate bone block, and wherein the tendon is secured between the first intermediate bone block and the second intermediate bone block of the second bone block assembly at the second end or at the second intermediate section of the tendon.

Figure 3C:
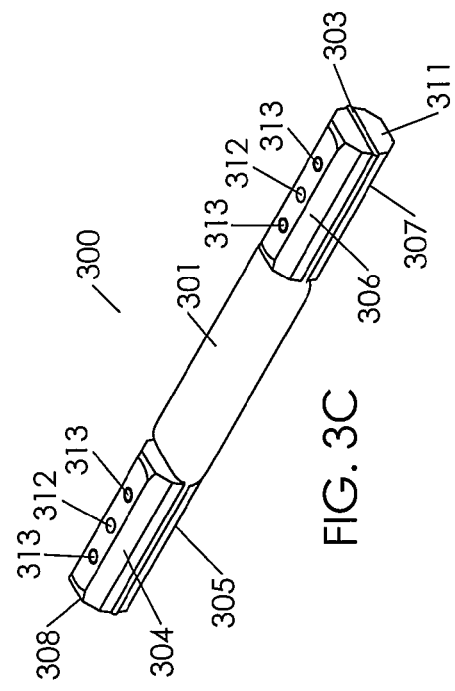
FIGS. 3A-3D are views of one embodiment of a bone-tendon-bone graft of the present technology having a tendon with an assembled bone block at each end.
Figure 3D:
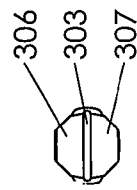
Figure 3B:
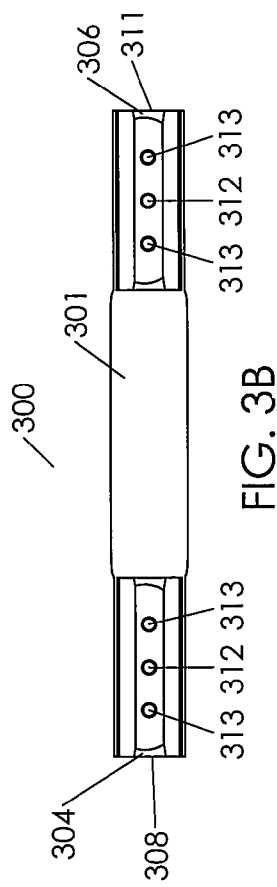
Figure 3A:
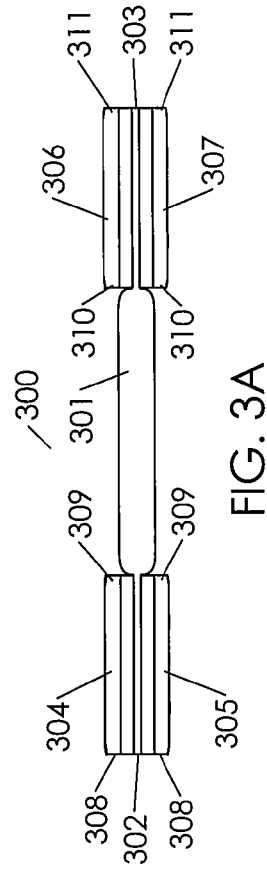

One example of such an embodiment is shown in FIGS. 3A-3D, which illustrate a bone-tendon-bone graft wherein the tendon is secured on either end by a bone block assembly comprising at least two intermediate bone blocks. FIG. 3A is a side view of implant 300 showing tendon 301 having a first end 302 secured by a first bone block assembly and a second end 303 secured by a second bone block assembly. The implant is shown with the bone block assemblies attached at the first and second ends, respectively, of the tendon. It should be noted that in certain embodiments (not shown), one or both bone block assemblies may be attached at the first or second intermediate section of the tendon, creating one or two tendon tails at either end of the implant. It should also be noted that the tendon is shown here in a relatively compact configuration for the sake of clarity, but that implants of the present invention may be made with many different sizes and types of tendons, including some which are larger in diameter or in effective diameter than their assembled or naturally attached bone blocks. As illustrated, the first bone block assembly comprises intermediate bone block 304 and intermediate bone block 305, and each intermediate bone block of the first bone block assembly has a distal end 308 and a proximal end 309. The second bone block assembly as illustrated in FIG. 3A comprises intermediate bone block 306 and intermediate bone block 307, and each intermediate bone block of the second bone block assembly has distal end 311 and proximal end 310.

FIG. 3B is a top view of implant 300. FIG. 3B shows that intermediate bone blocks 304 and 306 each have a center through-hole 312 and two through-holes 313. Intermediate bone blocks 305 and 307 preferably have through-holes that align with the through-holes of intermediate bone blocks 304 and 306, respectively. In preferred embodiments, through-holes 312 are graft manipulation holes and through-holes 313 each have a biocompatible connector inserted therein to connect the intermediate bone blocks to one another with the tendon secured therebetween.

As discussed above, any suitable biocompitable connector can be utilized to connect the intermediate bone blocks and secure the tendon therebetween. One particularly preferred type of biocompatible connector is a pin comprising cortical bone. Accordingly, in at least one embodiment of the present technology, the tendon is secured between the first intermediate bone block and the second intermediate bone block of the first bone block assembly by at least one pin comprising cortical bone; and wherein the tendon is secured between the first intermediate bone block and the second intermediate bone block of the second bone block assembly by at least one pin comprising cortical bone.

FIG. 3C is a perspective view of implant 300, illustrating tendon 301, a first bone block assembly comprising intermediate bone blocks 304 and 305, and a second bone block assembly comprising intermediate bone blocks 306 and 307. Second end 303 of the tendon is illustrated as being sandwiched between intermediate bone blocks 306 and 307, and can be seen at distal end 311 of the second bone block assembly. In the embodiment illustrated in FIG. 3C, the tendon is preferably secured between the intermediate bone blocks of the bone block assemblies by biocompatible connectors inserted into through-holes 313. FIG. 3D is an end view of implant 300 illustrating intermediate bone block 306 and intermediate bone block 307 having end 303 of the tendon secured therebetween.

At least some embodiments of BTB implants of the present technology comprising a first bone block assembly and a second bone block assembly can also provide a first grip on the tendon prior to implantation and a second grip on the tendon during or after implantation. The tendon of such an implant has a length, and the tendon comprises along its length at least a first end, a first intermediate section, a central section, a second intermediate section, and a second end. In such an embodiment, the first bone block assembly comprises at least a first intermediate bone block and a second intermediate bone block, and the tendon is secured between the first intermediate bone block and the second intermediate bone block of the first bone block assembly at the first end or at the first intermediate section of the tendon. Additionally, the second bone block assembly comprises at least a first intermediate bone block and a second intermediate bone block, and the tendon is secured between the first intermediate bone block and the second intermediate bone block of the second bone block assembly at the second end or at the second intermediate section of the tendon. In this type of embodiment, at least one of the first bone block assembly or the second bone block assembly provides a first grip on the tendon prior to implantation and a second grip on the tendon after implantation. In some embodiments, both the first bone block assembly and the second bone block assembly can provide a first grip on the tendon prior to implantation and a second grip on the tendon after implantation. The change in grip from a first grip to a second grip is preferably brought about by a controlled change in geometry, configuration, position or orientation of at least one of the intermediate bone blocks. The change from a first grip to a second grip on the tendon is alternatively brought about by either a symmetric or an asymmetric change in one or both of the two intermediate bone blocks.

Bone Components

Bone components suitable for use in the present technology can be made from non-synthetic materials (natural materials), synthetic materials, or combinations thereof. Some examples of synthetic materials from which bone components of the present technology can be made include, but are not limited to, hydroxyapitates, calcium phosphates, bioresorbable polymers, and bioresorbable ceramics. Bone components comprising natural materials can be derived from autograft, allograft or xenograft bone. Additionally, natural materials utilized in making bone components of the present technology can comprise cortical bone, cancellous bone, or both.

Bone components having a natural attachment to a tendon preferably comprises primarily cancellous bone, although a thin cortical shell or cap is typically located on the top surface of bone component at the naturally occurring attachment to the tendon. Bone components having a natural attachment to a tendon are preferably derived from a calcaneus bone and the attached Achilles' tendon, a tibial or patellar bone and attached patellar tendon, or a patellar bone and attached quadriceps tendon. Such bone components, and the tendons naturally attached thereto, are preferably allograft or xenograft.

Bone components utilized as bone components that are secured to a bone component having a natural attachment to a tendon, are preferably allograft or xenograft bone, and preferably comprise cortical bone. It may be desirable to secure a second bone component to a bone component having a natural attachment to a tendon for several reasons. In some instances, for example, bone components having a natural attachment to a tendon can be damaged or cut to smaller than desired dimensions during recovering and/or shaping procedures. Second bone components of the present technology can be used, for example, to repair, reshape, or support a first bone component. Second bone components can also be used add strength or provide other desirable design characteristics to the end of an implant having a natural tendon attachment. This is especially advantageous in cases where the donor bone block has less than desirable density, uniformity, or strength; or, where a localized defect renders a bone block and the naturally attached tendon unsuitable for use.

Bone components that are assembled to form bone block assemblies of the present technology are generally referred to herein as being intermediate bone blocks. For example, bone block assemblies of the present technology preferably comprise at least two intermediate bone blocks. Bone block assemblies can comprise more than two intermediate bone blocks, such as three, four, five, or more than five intermediate bone blocks.

Intermediate bone blocks of the present technology preferably comprise cancellous bone, cortical bone, or a combination of cancellous bone and cortical bone. Intermediate bone blocks of the present technology preferably comprise allograft or xenograft bone. In particularly preferred embodiments, intermediate bone blocks of the present technology comprise dense cancellous bone, which can be, for example, allograft or xenograft bone derived from subchondral bone, more preferably from subchondral bone just below a load bearing cartilaginous region of a long bone. Most preferably, the material for intermediate bone blocks is taken from regions of subchondral or dense cancellous bone, cortical-cancellous, or cortical bone. For example, bone components of the present technology, particularly bone components used as intermediate bone blocks can be derived from the humeral or femoral head, femoral condyles, tibial plateau, dital tibia, talus, patella or vertebral bodies.

When cancellous bone material is taken from non-human or xenograft donors, the cancellous bone has been observed to be denser, stiffer, and sometimes more brittle. It is contemplated in the present technology that xenograft cancellous bone material may be advantageously used in certain embodiments where the increased density and strength is beneficial. It is also contemplated that more dense or strong materials will require more features, such as stress concentrating features, to ensure their ability to achieve a second grip on the grafts as described. It is further contemplated that more dense or strong materials, including xenograft cancellous or cortical bone, may allow intermediate bone blocks with a shorter height to function similarly to normally sized blocks of human cancellous bone material. Thus, it is contemplated by the present invention that assembled grafts fitting smaller tunnels, such as an 8 mm or 9 mm tunnel for a pediatric patient, may be realized through the use of xenograft materials.

Any suitable method can be used for obtaining and forming bone components of the present technology. As illustrated in FIG. 14B, in at least one particularly preferred embodiment, bone blanks 1411 or bone plugs are recovered from a condyle 1410 such that they comprise cancellous bone having a cortical cap or shell 1413 on one surface 1415 thereof The bone blank or bone plug can then be shaped further so that the resulting bone component has the desired final shape and dimensions. In the process of shaping the bone blank or bone plug, the cortical cap is optionally completely, partly, or substantially removed. When the cortical cap is completely removed, the dense cancellous material just below the cortical cap provides a firm structure which tends to crush evenly under the insertion of an interference screw. In this case, the cancellous matrix itself provides a stress concentrating feature, allowing the intermediate bone block to break free from the vertical hold of the pins and compress farther into the tendon to provide a second grip on the tendon following implantation. When the cortical cap is partly removed, the remaining cortical regions may be advantageously configured to provide support for, or to enhance the function of, a stress concentrating feature. In one such embodiment, the cortical shell is partly removed from the center of the intermediate bone block, but not removed from the long edges of the intermediate bone block, thus providing a cancellous bone channel which may readily accept an interference screw while concentrating stress to a break point along the center of the intermediate bone block. When the cortical cap is substantially removed, the resulting intermediate bone block is primarily dense cancellous material with possibly a few areas of hard cortical bone still attached.

In another particularly preferred embodiment, the bone blanks are preferably removed from the dense cancellous material of the subchondral bone, just below the cortical bone cap in a load bearing cartilaginous region of a long bone. Some preferred embodiments of the present technology make advantageous use of the available dense cancellous material, which tends to be more dense, stronger, more consistent, and under less demand for use in other graft applications such as assembled spinal implant constructs due to its thin shape and due to the natural curvature found in the cancellous cap in many of these regions. FIG. 14A shows how a bone blank 1401 may be preferably recovered from an orientation where the tendon engaging surface 1402 of the resulting bone component is farther from the cortical cap 1403 and facing into the open cancellous area 1404 inside the bone. Correspondingly, such bone blanks are also recovered from an orientation where the outer surface 1405, or interference screw engaging surface in some embodiments, is nearer the cortical cap and faces toward the cortical cap. This provides for more dense, tighter, stronger cancellous material on the outer surface, and less dense, more open, larger pore size material on the tendon engaging surface. It is believed that this orientation facilitates better fixation and higher pullout strength values by providing a stronger area of material on the outer surface to support fixation and a more open textured material on the tendon engaging surface to better grip the tendon.

Alternatively, the bone blanks can be recovered from an orientation such that the cortical cap is retained on a portion of either the outer surface or the tendon engaging surface of the intermediate bone block as shown in FIG. 14B. This cortical cap may be advantageously configured to provide desired strength, rigidity, or material for machining of complex geometric features, such as stress concentrating features. The cortical cap can provide added structure and open new design options over a purely cancellous intermediate bone block, making this configuration more desirable in cases where those design features are highly valued, as in the completion of a few or up to a hundred similar grafts where design features may be selected from the available material and where supply and yields are both sufficient to produce the required grafts. Substantially cancellous bone blocks may be preferable in cases where consistency, availability, and uniformity of the finished bone blocks take precedence, or where geometric shape of the interface between cortical and cancellous bone might present problems in constructing the grafts. Examples of these scenarios include high volume or supply constrained manufacturing to a common required design specification, where the substantially cancellous bone blocks may be cut and shaped to a more predictable starting point for manufacturing, thus finally producing more consistently shaped and featured grafts.

When multiple intermediate bone blocks are assembled to form a bone block assembly of the present technology, the intermediate bone blocks can comprise materials that are the same or different. For example, in some embodiments of bone block assemblies comprising a first intermediate bone block and a second intermediate bone block, the first intermediate bone block comprises cancellous bone and the second intermediate bone block comprises cortical bone. In other embodiments, the first intermediate bone block comprises cancellous bone and the second intermediate bone block comprises cancellous bone. While intermediate bone blocks that are assembled to form bone block assemblies can comprise any combination of materials suitable for the end use application, in particularly preferred embodiments, each intermediate bone block of a bone block assembly comprises material derived from a single source, such as bone from a single donor.

Bone components of the present technology, such as intermediate bone blocks, can be from about 15 mm to about 35 mm in length, as measured from the proximal end to the distal end, or vice versa. More preferably, bone components of the present technology are from about 20 mm to about 30 mm long, and most preferably from about 23 mm to about 27 mm long. For example, some particularly preferred intermediate bone blocks of the present technology can be 23 mm, 24 mm, 25 mm, 26 mm, or 27 mm long.

The height of bone components of the present technology is constrained by the limitations on the effective diameter of the final implant. The effective diameter of a BTB implant is the widest non-yielding distance across the implant. In embodiments of the present technology a bone block assembly has a tendon sandwiched and secured between two intermediate bone blocks, for example, the effective diameter is typically the widest distance measurable from the outer surface of the first intermediate bone block to the outer surface of the second intermediate bone block after the implant has been assembled. The effective diameter thus typically includes the maximum height of each intermediate bone block, as well as the thickness of the tendon, which is preferably in a compressed state secured between the intermediate bone blocks. The bone tunnel into which the BTB is implanted tends to be relatively circular, and is typically from about 8 mm to about 14 mm in diameter. For example, a femoral or tibial bone tunnel is most commonly from about 9 mm to about 12 mm in diameter, but diameters up to about 14 mm or larger are not uncommon, particularly in instances of revision procedures.

Bone components of the present technology preferably have a maximum height that allows an assembled BTB implant of the present technology to be inserted into the desired bone tunnel. Accordingly, bone components of the present technology preferably have a maximum height of from about 1 mm to about 10 mm. More preferably, bone components of the present technology preferably have a maximum height of from about 2 mm to about 8 mm, and most preferably from about 3 mm to about 6 mm. For example, some preferred embodiments of intermediate bone blocks of the present technology have a maximum height of 3 mm, 4 mm, 5 mm or 6 mm. Bone components that are assembled with one another, such as intermediate bone blocks that are assembled to form a bone block assembly, can have maximum heights that are the same or different. In particularly preferred embodiments where a bone block assembly comprises two intermediate bone blocks, each bone block has the same maximum height.

The width of bone components of the present technology is also constrained by the limitations on the nominal diameter of the final implant, as determined by the desired nominal diameter of the surgical implantation tunnel size. In the case of an assembled bone block, the effective diameter of the graft may be defined as the diameter of the smallest circle capable of completely circumscribing the bone block assembly profile. It is often convenient to discuss graft components relative to the nominal, or designed dimensions of the graft or of the corresponding surgical bone tunnel, so that dimensions may be considered as relative to the driving dimensions of nominal diameter or nominal gauge length. Bone components of the present technology are typically from about 1 mm more in width to about 1 mm less in width, and preferably from about 0 mm to about 0.5 mm less in width than the effective nominal diameter of the finished graft for which they are designed. For example, some preferred embodiments of intermediate bone blocks of the present invention have a width of about 8.5 mm, 9.5 mm, 10.5 mm, 11.5 mm, 12.5 mm, or 13.5 mm. Intermediate bone blocks of the present invention are typically between about 7 mm and about 14 mm wide, preferably between about 8 m and about 12 mm wide, and more preferably between about 9 mm wide and about 11 mm wide. In the case of a tendon with a non-circular cross section, such as flat, rectangular, or irregular; the effective diameter of the tendon can be defined as the diameter of a circle having the same cross sectional area as that of the actual tendon cross section. Both tendons and bone blocks (assembled or otherwise) may be discussed in terms of effective area, or an equivalent effective diameter. Intermediate bone blocks of the present invention typically have a width of at least about 70% of the effective diameter of the bone block assembly, preferably at least about 80%, more preferably at least about 90%, most preferably at least about 95%.

Figure 4C:
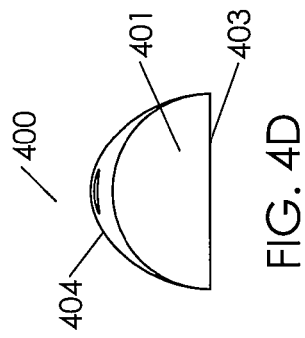
FIGS. 4A-4D are views of one embodiment of an intermediate bone block for use in an assembled bone block of the present technology.
Figure 4D:
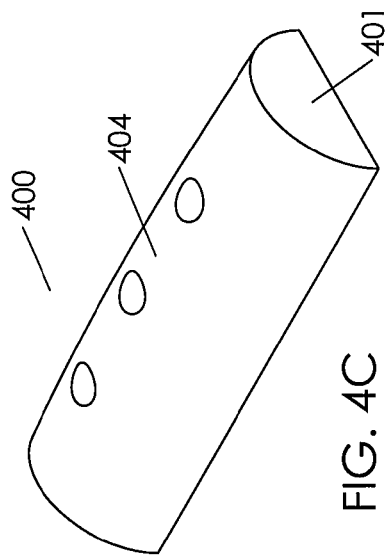
Figure 4B:
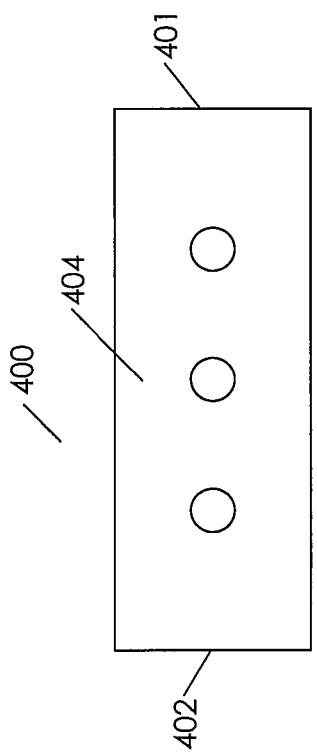
Figure 4A:
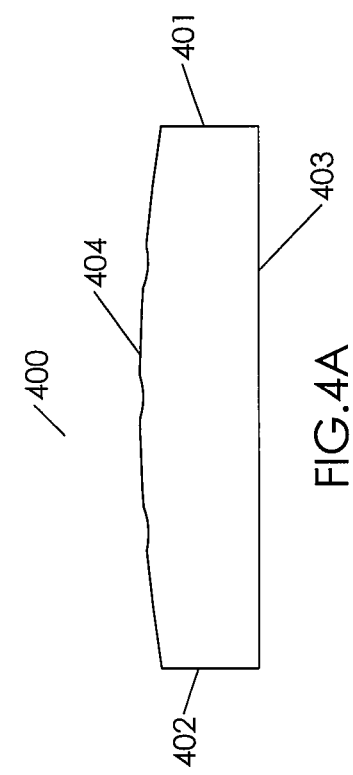

FIGS. 4A-4D are views of one embodiment of an intermediate bone block for use in an assembled bone block of the present technology. FIG. 4A is a side view of intermediate bone block 400 having proximal end 401, distal end 402, tendon engaging surface 403, and top surface 404. As shown, top surface 404 of intermediate bone block 400 is arched, having a maximum height at the center of the intermediate bone block that tapers down towards the ends of the intermediate bone block. The height of the intermediate bone block can be constant from the proximal end to the distal end, or could vary in a manner different from the arch illustrated in FIG. 4A. For example, the intermediate bone block could be tapered, with a maximum height at one end and a minimum height at the other end.

FIG. 4B is a top view of intermediate bone block 400, showing top surface 404, proximal end 401 and distal end 402. Also illustrated in FIG. 4B are three through-holes in top surface 404. In the view of FIG. 4B, the outer perimeter of intermediate bone block 400 is rectangular. In other embodiments, the outer perimeter of the intermediate bone block could be any suitable shape, such as having rounded edges or rounded corners.

FIG. 4C is a perspective view of intermediate bone block 400, showing top surface 404 and proximal end 401. In this view, the end profile of proximal end 401 is a semi-circle. An intermediate bone block of the present technology can have any suitable end profile, and some examples of other end-profiles are provided in other figures. FIG. 4D is an end view of intermediate bone block 400, showing proximal end 401 having a semi-circular end-profile. Also illustrated in FIG. 4D are top surface 404 tapering down to proximal end 401, and tendon engaging surface 403.

Figure 5C:
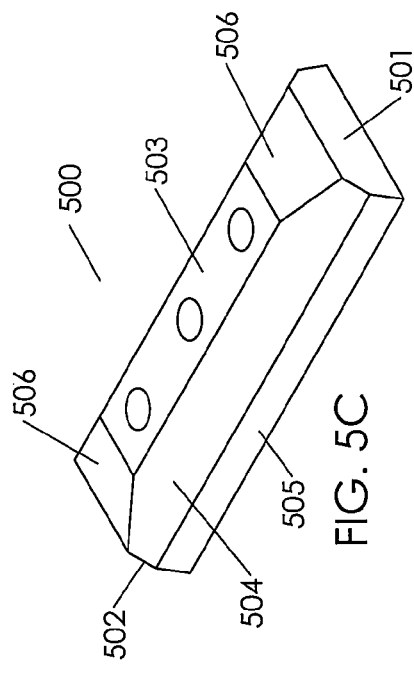
FIGS. 5A-5D are views of one embodiment of an intermediate bone block for use in an assembled bone block of the present technology.
Figure 5D:
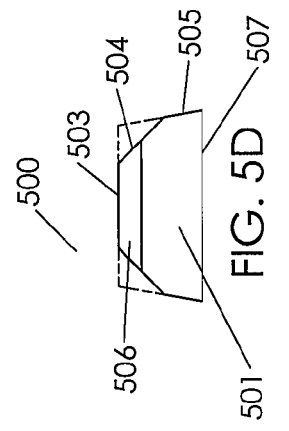
Figure 5B:
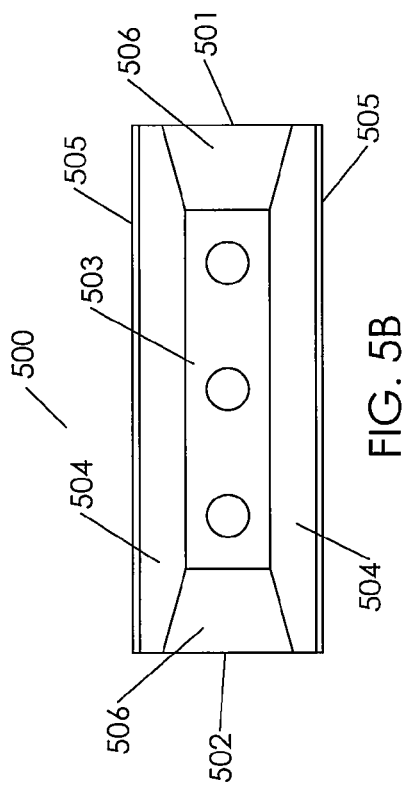
Figure 5A:
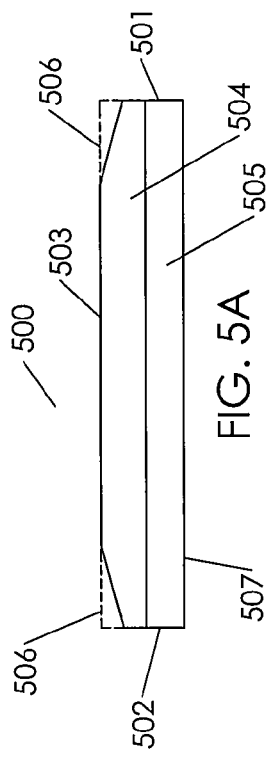

FIGS. 5A-5D are views of another embodiment of an intermediate bone block of the present technology. As illustrated, intermediate bone block 500 has top surface 503 with optionally tapered or chamfered edges 504 and optionally tapered or chamfered ends 506. FIG. 5A is a side view of intermediate bone block 500 illustrating that ends 506 of outer surface 503 can be optionally tapered or chamfered. As illustrated in FIG. 5A, edges 504 of top surface are tapered or chamfered such that the height of the intermediate bone block decreases towards side portion 505. FIG. 5A also illustrates tendon engaging surface 507, proximal end 501 and distal end 502.

FIG. 5B is a top view of intermediate bone block 500 illustrating that as viewed from above, the intermediate bone block has a generally rectangular outer perimeter. Also illustrated in FIG. 5B are three through-holes in the top surface 503 of intermediate bone block 500. FIG. 5C is a perspective view of intermediate bone block 500, and FIG. 5D is an end view of intermediate bone block 500. FIGS. 5C and 5D illustrate that the end profile of proximal end 501 is a modified half octagon. The term modified is used to describe the half octagon because side portions 505 are at an angle rather than being vertical. In other embodiments, the end profile could be a half hexagon having vertical sides. FIG. 5D also illustrates that edges 504 are optionally chamfered or tapered.

In one particularly preferred embodiment of the present technology, the intermediate bone blocks of the bone block assembly are shaped cancellous bone components having the configuration illustrated in FIGS. 5A-5D. The term shaped cancellous bone component contemplates that the bone component comprises design features which are preferably shaped by hand, more preferably without power tools, alternatively with only small handheld power tools, and most preferably shaped without the use of expensive and complicated equipment such as computer controlled machining centers or computer controlled lathes. For example, in one particularly preferred embodiment a shaped cancellous intermediate bone block of the present technology designed to be part of a bone block assembly for a graft with a 10 mm nominal diameter is about 4 mm tall, by about 9.5 mm wide, by about 25 mm long, with a long straight, rectangular body profile, no precision machined features, and a simple chamfered rectangular cross section. In other embodiments shaped cancellous intermediate bone block of the present technology designed to be part of a bone block assembly can have any suitable shape and dimensions as described herein, such as the half round shape illustrated in FIGS. 4A-4D.

Intermediate bone blocks of the present technology can have any suitable end profile. For example, FIGS. 6A-6G are end views of various embodiments of intermediate bone blocks. FIG. 6A is an end view of one embodiment of a intermediate bone block having a semi-circular end profile, having top surface 601 and tendon engaging surface 602. FIG. 6B is an end view of one embodiment of a intermediate bone block having an end profile that is a circular segment less than a semi-circle, having top surface 603 and tendon engaging surface 604. FIG. 6C is an end view of one embodiment of a intermediate bone block having an end profile that is a gibbous circular segment, or circular segment greater than a semi-circle, having top surface 605 and tendon engaging surface 606. FIG. 6D is an end view of one embodiment of a intermediate bone block having an end profile that is a modified half octagon, having top surface 607 and tendon engaging surface 608. FIG. 6E is an end view of one embodiment of a intermediate bone block having an end profile that is half of a dodecagon or a modified dodecagon, having top surface 609 and tendon engaging surface 610. FIG. 6F is an end view of one embodiment of a intermediate bone block having a triangular end profile, having top surface 611 and tending engaging surface 612. The triangular profile illustrated in FIG. 6F is a right triangle, with the angle in top surface 611 being 90°. In other embodiments a triangular end profile could be an acute triangle, such as an isosceles triangle, or an obtuse triangle. FIG. 6G is an end view of one embodiment of a intermediate bone block having a rectangular end profile, having top surface 613 and tendon engaging surface 614. The embodiments illustrated in FIGS. 6A-6G are illustrative only, and should not be interpreted as limiting the shape of the end profile of an intermediate bone block of the present technology.

Intermediate bone blocks of the present technology, particularly first and second intermediate bone blocks in a bone block assembly comprising only two intermediate bone blocks, preferably comprise an outer surface and a tendon engaging surface. The outer surface of an intermediate bone block is the surface farthest from the tendon when the intermediate bone blocks are assembled into a bone block assembly having a tendon sandwiched between the intermediate bone blocks. When a BTB of the present technology is implanted in a patient, the outer surface generally engages either the bone tunnel of the patient and/or a fixation device, such as an interference screw. The tendon engaging surface of an intermediate bone block of the present technology is the surface that engages the tendon and provides grip on the tendon to resist or prevent tendon slippage.

The tendon engaging surface of an intermediate bone block of the present technology can comprise a textured surface. For example, in embodiments of the present technology having a bone block assembly comprising at least a first and a second intermediate bone block, the first intermediate bone block comprises an outer surface and a tendon engaging surface, the second intermediate bone block comprises an outer surface and a tendon engaging surface, and the tendon engaging surface of at least one of the first intermediate bone block or the second intermediate bone block comprises a textured surface.

A textured surface on a tendon engaging surface an intermediate bone block of the present technology can be a natural texture or a machined texture. A natural texture includes any texture that is naturally presented by the material from which the intermediate bone block is made. In embodiments where the intermediate bone block is shaped by cutting the material from which it is made, the natural texture of the material is the texture naturally presented by a cross section of the material. For example, molded synthetic materials tend to have a smooth or flat texture. Similarly, cortical bone, and cross-sections thereof, also tend to have a smooth or flat texture. Cancellous bone, and cross sections thereof, tends to have natural texture that is rough. In some embodiments of the present technology, the tissue engaging surface of an intermediate bone block has a textured surface comprising the natural texture of a cross section of the cancellous bone or the natural texture of a cross section of cortical bone.

Machined textures can be formed on intermediate bone blocks through careful application of conventional machining methods known in the art, using milling machines, lathes, router tables and the like. Some examples of machined textures that can be formed on intermediate bone blocks of the present technology include, but are not limited to, sawteeth, crosscut diamond peaks, ridges, gripping channels, gear grips, slots, and combinations thereof. Sawteeth are preferably angled against the pull of the tendon, having their peaks towards the proximal end of the intermediate bone block and their slopes towards the distal end. Gear grips are a series of raised and lowered areas oriented across the width of an intermediate bone block that preferably compress a tendon and mate with opposing lowered and raised areas on another intermediate bone block, respectively, when the two intermediate bone blocks are assembled in a bone block assembly.

Gripping channels are one particularly preferred texture. For example, in some embodiments of the present technology an intermediate bone block has a tissue engaging surface that comprises at least one gripping channel. Gripping channels are channels that can be cut in any direction, such as lengthwise or crosswise, in a tissue engaging surface. The areas of the tissue engaging surface that do not have channels running therethrough can be referred to as compression surfaces. A gripping channel can traverse the entire length or width of an intermediate bone block, or only part of the length or width. The tissue engaging surface of an intermediate bone block of the present technology can have more than one gripping channel, and can have more than one gripping channel traversing its length and more than one gripping channel traversing its width.

For example, in at least one embodiment, a tissue engaging surface comprises two gripping channels traversing the length of the intermediate bone block and three gripping channels traversing the width of the intermediate bone block. One embodiment if such an intermediate bone block is illustrated in FIGS. 7A-7D. The gripping channels as illustrated in FIGS. 7A-7D have a "U" shaped cross-section. FIG. 7A is a side view of intermediate bone block 700, showing proximal end 701, distal end 702, outer surface 703, and a tendon engaging surface comprising tissue compression surfaces 704 and gripping channels 705. FIG. 7B is a direct view of the tissue engaging surface of intermediate bone block 700, showing tissue compression surfaces 704, two gripping channels 706 traversing the length of the intermediate bone block, and three gripping channels 705 traversing the width of the intermediate bone block. FIG. 7C is a perspective view of intermediate bone block 700, showing proximal end 701, tissue compression surfaces 704, two gripping channels 706 traversing the length of the intermediate bone block, and three gripping channels 705 traversing the width of the intermediate bone block. FIG. 7D is an end view of intermediate bone block 700, showing proximal end 701, top surface 703, and two gripping channels 706.

Gripping channels can have any suitable cross-sectional profile, including, but not limited to, rectangular, square, semi-circular, semi-ovular, triangular, trapezoidal, sinusoidal, curvilinear, dovetail, omega, or a combination thereof. The omega profile channels developed by the applicants were found to be preferable in working with previous assembled bone block designs, and may still be considered preferable for use with the intermediate bone blocks of the present invention. One surprising benefit of certain embodiments of the present invention is that the omega channels, while still preferable, are not always required to achieve acceptable performance with the designs of the present invention. Gripping channels can also form crossed or curved patterns in the tissue engaging surface of an intermediate bone block, such as waves, "S" shapes, zigzags, "V" shapes, overlapping "V" shapes, "U" shapes, overlapping "U" shapes, "X" shapes, overlapping "X" shapes, or any other pattern. Without being bound by any particular theory, it is believed that tendons, or at least portions thereof, flow into and tend to fill gripping channels when the tendon is compressed between intermediate bone blocks in a bone block assembly, and that the grip on the tendon is thereby enhanced.

When bone block assemblies of the present technology comprise two intermediate bone blocks, one or both of the intermediate bone blocks can have a textured surface. In some such embodiments, the second intermediate bone block can comprise a textured tendon engaging surface that is the same as the texture of the tendon engaging surface on the first intermediate bone block. In other embodiments, the second intermediate bone block can comprise a textured tendon engaging surface that is different from the texture of the tendon engaging surface on the first intermediate bone block.

Altering the Grip of Bone Block Assemblies

It has been surprisingly discovered that assembled implants that grip a tendon can have improved performance when they are designed and configured such that the nature of the grip on the tendon changes from its pre-implantation state to its post-implantation state, while the general location and orientation of the bone block assemblies relative to the tendon is maintained at about the same position in at least one dimension. Accordingly, in one aspect, the present technology relates to an implant comprising a tendon and a bone block assembly comprising at least a first intermediate bone block and a second intermediate bone block, wherein the bone block assembly has a first grip on the tendon prior to implantation of the implant into a patient and a second grip on the tendon after implantation of the implant into a patient.

Because the forces that are exerted upon a tendon by an intermediate bone block or a bone block assembly of the present technology can include, but are not limited to, compressive, frictional, tensional, and rotational forces, a change in the grip that a bone block assembly has on the tendon can be brought about by altering any of these types of forces. For example, in some preferred embodiments, the first grip of the bone block assembly on the tendon provides one level of compression to the tendon prior to implantation of the implant into a patient, and the second grip provides a second level of compression to the tendon after implantation of the implant into a patient. In at least one such embodiment, the tendon is compressed between the first intermediate bone block and the second intermediate bone block of a bone block assembly, and the tendon is subject to further compression by the bone block assembly during implantation of the graft. The further compression can be exerted, for example, to establish fixation of the graft, such as by the insertion of an interference screw.

Another example of a manner in which the grip of a bone block assembly on a tendon can be changed is that the geometric configuration of a bone block assembly can change from its initial or first configuration prior to implantation to a second configuration during implantation. The geometric configuration of a bone block assembly can be changed, for example, by altering the geometric configuration of one or more of the intermediate bone blocks that form the bone block assembly, or by altering the spatial relationship between at least a first intermediate bone block and at least a second intermediate bone block in a bone block assembly.

With respect to embodiments that provide an altering of the spatial relationship between at least a first intermediate bone block and at least a second intermediate bone block in a bone block assembly, in some such embodiments, the tendon is secured between the first intermediate bone block and the second intermediate bone block at a fixed location along its length, such as the first end, the first intermediate section, the second intermediate section, or the second end of the tendon. The tendon is preferably secured by at least one biocompatible connector that is inserted into an aligned set of through-holes in the intermediate bone blocks. One particularly preferred type of biocompatible connector is a rigid pin. Rigid pins can made of metal, synthetic material, or cortical bone. Additionally, a rigid pin preferably forms an interference fit with the through-hole into which it is inserted. Rigid pins can be shaped or configured in such a manner that they allow the intermediate bone blocks to shift in one or two dimensions during implantation, while preferably maintaining the fixed location of the bone block assembly along the third dimension, such as along the length of the tendon.

Some examples of such rigid pin configurations include, but are not limited to loose pins, stepped pins, reverse-tapered pins, break-away pins, asymmetric pins, mismatched pins, or demineralized pins.

Loose pins are those which fit into mating holes with sufficient interference to hold them in place during handling, processing, sterilization, packaging, unpackaging, surgical prep, or insertion; but which then allow for a change in configuration, preferably increased compression, during fixation, preferably with an interference screw. The exact dimensions required for a given application may be determined by experimentation, following teachings known in the art, including methods particularly suited to creating tight interference fits with cortical bone pins disclosed in commonly assigned US Patent Application Publication Nos. 20040115172 and 20060229722 which are incorporated here by reference for their specific disclosure regarding the manufacture and sizing of precision fit bone pins.

Stepped pins are those which have a collar or step feature of increased diameter at one end, configured and adapted with or without a mating feature in the intermediate bone block to allow movement of the intermediate bone block in one direction only from a given point. These constructs are commonly known in the machine design or mechanical arts, and are preferably configured as a single step preventing separation of the intermediate bone blocks, while allowing compression. Stepped pins may also be configured to with more than one step to control movement of the block over a range or over different areas.

Reverse tapered pins are similar to stepped pins, but instead of a stepwise increase in diameter, they exhibit a gradual increase, thus providing a more controlled hold and release of the intermediate bone block in the desired direction.

Breakaway pins are designed to break, crack, deflect, or fracture either wholly or partially upon or after fixation of the graft. In some embodiments breakaway pins include a notch, cut or hole which predisposes them to break at a predetermined point under a specified load. In one embodiment breakaway pins include a cut located at or near the tendon engaging surface of one intermediate bone block, configured and dimensioned to allow the pin to shear off upon insertion of an interference screw across the outer end of the pin.

Asymmetric or mismatched pins are variations on the theme of a square peg in a round hole. In some embodiments they include an asymmetric oval shape configured and adapted to press unevenly into a round hole. In other embodiments they include square, rectangular or other polygonal cross sections configured and dimensioned to press fit into a round hole. In further embodiments the pins are round, but configured and adapted to press fit into a non-round hole, such as a broached square or offset oval shape.

Rigid pins for use in a bone block assembly of the present invention are preferably from about 0.5 mm to about 5 mm in diameter, more preferably from about 1 mm to about 3 mm in diameter, and most preferably from about 1.5 mm to about 2 mm in diameter. When such rigid pins are made from cortical bone, smaller size pins are more efficient in use of bone material, but more difficult to manufacture and use reliably, especially in high volume, due to their fragile nature. Larger pins are stronger and easier to work with, although they require larger quantities of bone to manufacture, and larger mounting holes and bone blocks to assemble.

When rigid pins are made of cortical bone, they may be either fully mineralized fully demineralized or partially demineralized. Demineralization is well known in the art typically removes calcium by treatment of bone with an acid, reducing the rigidity and brittleness of the bone, while increasing its flexibility and toughness. It is well known and established in the art that partial demineralization can be controlled to produce a bone construct, including a pin, that is very lightly demineralized and similar in properties to fully mineralized bone, lightly demineralized, moderately demineralized, heavily demineralized, or very heavily demineralized, having greatly reduced strength and greatly increased flexibility. Treatment methods and resulting measures of demineralization by net percentage, by volume, or by depth of penetration are well known in the art.

It is noted that a fully demineralized or heavily demineralized bone pin is still referred to herein as a rigid connector, despite having a higher degree of flexibility. This is to distinguish the bone pin, which still holds its basic shape while flexing, from truly flexible connectors such as suture, tape, or engineered synthetic constructs which are capable of wrapping around, tying in knots, or flexing into shapes dissimilar from their original configuration.

When biocompatible connectors, including pins, are placed into holes, the holes may be either through holes traversing the entire width, length or thickness of the graft or of one component, such as an intermediate bone block, as shown in FIGS. 1-5. Alternatively, the holes may be blind holes passing through only one outer surface of the graft or of any one component such as an intermediate bone block, as shown in FIG. 15.

FIGS. 15A-D illustrate preferred configurations by which biocompatible connectors, such as bone pins, may be used to fasten a first intermediate bone block to a second intermediate bone block.

Figure 15C:
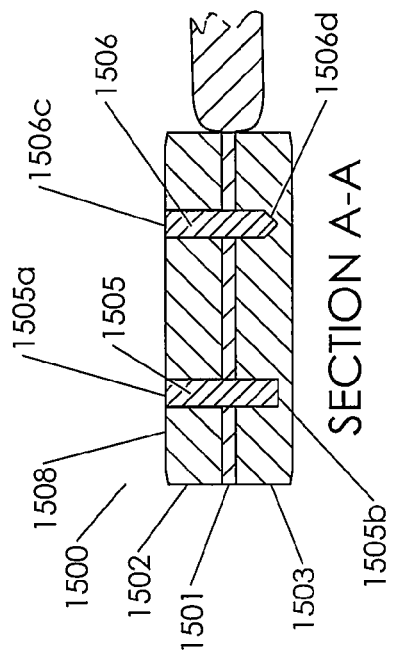
FIGS. 15A-15D illustrate various embodiments of pinning using pointed or flat pins in either pointed of flat bottom blind holes or through holes.
Figure 15D:
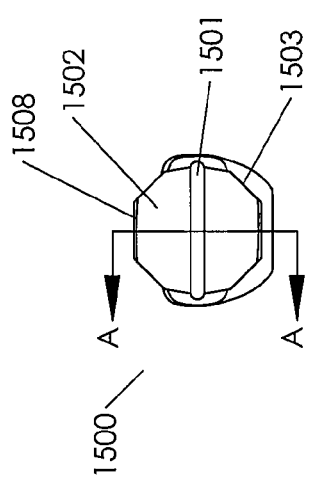
Figure 15B:
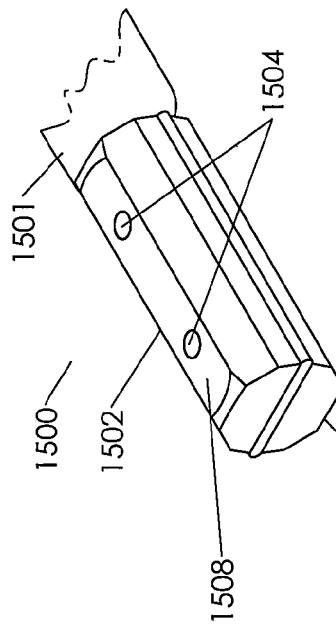
Figure 15A:
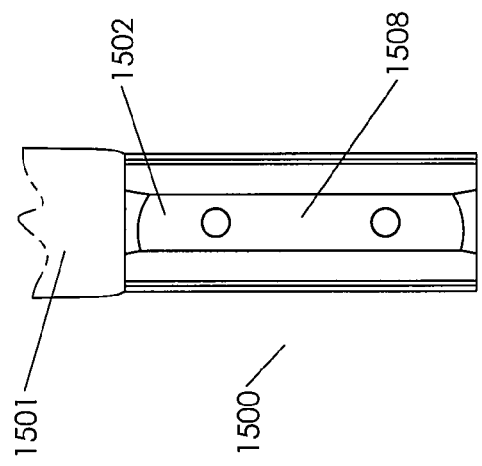

FIG. 15A is an end view of an assembled bone-tendon graft, showing the bone block assembly 1500 and the location of section A-A.

FIG. 15B is a top view of a bone block assembly, showing the tendon 1501 emerging from one end of the bone block assembly 1500, and a first intermediate 1502 bone block with two mounting holes 1504 drilled into the top surface 1508 to receive connectors. For simplicity, optional tendon tail and graft manipulation holes are not shown.

FIG. 15C is a perspective view of the assembled bone block and tendon, showing the mounting holes 1504 entering through the top surface 1508.

The cross section A-A of FIG. 15D illustrates several possible end conditions for a bone pin. In one preferred embodiment both ends of a bone pin 1505 are flat, the first end 1505*b* of the bone pin 1505 rests fully bottomed within a blind hole, while the second end 1505*a* of the bone pin 1505 is cut off flush with the top surface 1508 of the bone block assembly. Alternatively, end 1505*b* may rest just above or shorter than the bottom of the corresponding blind hole. Alternatively a flat ended pin 1505 may rest in an angle-bottomed hole such as the hole shown for pin 1506. In another embodiment a bone pin 1506 is sharply pointed or sharpened to a moderate level or rounded to a small radius to allow the bone pins to push through and separate the tendon fibers during assembly. The first end 1506*d* of pin 1506 is shown resting fully bottomed in a matching sharp pointed blind hole in second intermediate bone block 1503, while the first end 1506*c* is cut off flush with top surface 1508. Alternatively, end 1506*d* may rest just above or shorter than the bottom of the corresponding blind hole. Alternatively a sharp ended pin 1506 may rest in an flat-bottomed blind hole such as the hole shown for pin 1505. Pins may preferably be ground or cut off flush with an outer surface of a bone block assembly to facilitate insertion and graft handling, or alternatively remain protruding above the surface to provide a desired surgeon, instrument or patient interface. In certain embodiments, pins may be made short and pressed in to a recessed position below the top surface 1508.

One or both intermediate bone blocks may feature blind or through holes or both. A pin may be pressed into a through hole on one side and a blind hole on the other, or into two through holes, or in between two blind holes, trapping the pin fully inside the graft. Sharp, rounded or flat ended pins are contemplated for use with through holes, partial through holes, or blind (non-through) holes. Pointed, rounded, or sharp pins have the advantage of being able to separate the tendon fibers without additional tooling, fixtures or manipulation, but the disadvantage of requiring more material in the tapered section which may not provide any better mounting of the tendon and bone blocks. Blind or through holes are contemplated alone or in combination for use with sharp, rounded or flat ended pins. Through holes provide advantages in ease of manufacturing, design tolerance insensitivity and simplicity of design. Blind holes provide advantages in structural integrity, look feel and finish of the graft, and smooth, uninterrupted outer surfaces for graft insertion.

Any combination of the above described pin elements is contemplated within the scope of the present invention. For example, one embodiment may have demineralized pins which are stepped and tapered, then configured and adapted to flex or break at a predetermined location along the pin upon insertion of an interference screw.

With respect to embodiments that provide an altering of the geometric configuration of one or more of the intermediate bone blocks that form the bone block assembly, some examples of the manner in which the geometric configuration can change include an intermediate bone block flexing, bending, crushing, compressing, or separating.

For example, in some preferred embodiments of BTB implants of the present technology, at least one intermediate bone block of one bone block assembly comprises a stress concentrating feature. Accordingly, in some preferred bone block assemblies of the present technology that comprise a first intermediate bone block and a second intermediate bone block, the first intermediate bone block comprises an outer surface and a tendon engaging surface, the second intermediate bone block comprises an outer surface and a tendon engaging surface, and at least one of the first intermediate bone block or the second intermediate bone block has a modified outer surface, wherein the modified outer surface comprises a stress concentrating feature. In certain embodiments, two intermediate bone blocks of one bone block assembly each comprise a stress concentrating feature, wherein the stress concentrating features are the same as, or alternatively, different from each other. Identical stress concentrating features may be advantageously configured to ensure a symmetric graft, facilitating ease of insertion and simplifying surgical technique. Different stress concentrating features may be advantageously configured between two intermediate bone blocks of one bone block assembly to provide a controlled grip or change in grip upon fixation. For example, in a preferred embodiment, a notched groove may help guide an interference screw into place along one intermediate bone block while bringing about a controlled break, crack or separation upon fixation with the interference screw; while a series of saw cuts or ridges may improve the interface between graft and bone tunnel on the opposite side of the tendon while bringing about a controlled break, crack, or separation on the second intermediate bone block. Alternatively, the stress concentrating feature on the second intermediate bone block in a bone block assembly may be configured to break, crack or separate only at a substantially higher load level than the stress concentrating feature on the first intermediate bone block in the same bone block assembly. For example, a notched groove may be configured to break away on the first intermediate bone block under expected loading from an interference screw, while a series of saw cuts or ridges on the second intermediate bone block may be configured to break, crack or separate the second intermediate bone block only if twice the expected load is achieved. While stress concentrating features can be used on intermediate bone blocks comprising any suitable material, in particularly preferred embodiments, an intermediate bone block having a stress concentrating feature comprises cortical bone.

Stress concentrating features are features designed to focus, direct, or otherwise concentrate forces exerted on the intermediate bone block during implantation. Examples of forces exerted on an intermediate bone block during implantation include, for example, pressures and compressive forces exerted by a bone tunnel or by a fixation device such as an interference screw. A stress concentrating feature preferably concentrates the forces exerted on an intermediate bone block during implantation at a predetermined location, and the intermediate bone block preferably undergoes a change in its geometric configuration as a result, such as flexing, bending, or separating. Stress concentrating features on the outer surface of an intermediate bone block can be particularly effective when used in conjunction with textured surfaces on the tendon engaging surface.

Some examples of stress concentrating features of the present technology include, but are not limited to a notched groove, a truncation, a series of notches, or a demineralized area. A notched groove may be located at the center of the length of an intermediate bone block, alternatively may be located near or at one or both ends of an intermediate bone block, or preferably traverses the entire length of an intermediate bone block, and can have any cross-sectional profile suitable for the desired amount of stress concentration and the desired location of the stress concentration. For example, in some embodiments, a notched groove has a cross section comprising a V-shape, a semi-circle, a U-shape, a triangular shape, an arcuate shape, a curvilinear shape, or a rectilinear shape. Furthermore, in some particularly referred embodiments, a notched groove is dimensioned and configured to engage an interference screw upon implantation of the implant into a patient. For example, a notched groove running the entire length of the intermediate bone block may be advantageously configured to guide an interference screw along the center of the graft. A notched groove running along the center or either end of the intermediate bone block may be advantageously configured to provide resistance or guidance to an interference screw at a particular point along the length of the intermediate bone block. A notched groove with a constant cross sectional profile may be advantageously configured to provide constant guidance and resistance to an interference screw on insertion, and also provide more consistent and controlled stress or stress concentration to the intermediate bone block. A notched groove with a variable cross sectional profile may be advantageously configured to provide variable guidance and resistance to an interference screw on insertion, and also provide variable stress or stress concentration to the intermediate bone block. A truncation is typically a flat cut that removes material from the top of an intermediate bone block, and can be thought of as a flat notch. A series of notches is a set of notches that form a pattern on the top surface of an intermediate bone block. For example, a series of notches could form a dotted line that substantially traverses the length of an intermediate bone block. Each notch in a series of notches can be any shape or depth suitable for the desired amount of stress concentration and the desired location of the stress concentration. A demineralized area is any area of an intermediate bone block that has been demineralized or partially demineralized. Demineralization technology is sufficiently advanced to allow for demineralization of very precise areas of bone, including patterns of demineralization on an intermediate bone block. For example, a strip of demineralized or partially demineralized bone could be made that traverses the length of an intermediate bone block. The demineralized area can constitute the entire height of an intermediate bone block, or less than the entire height, but preferably constitutes at least about half of the height of the intermediate bone block. It should be understood that other stress concentrating features or means of causing a change of geometry in an intermediate bone block beyond the specific embodiments detailed herein are contemplated for use in the design and construction of intermediate bone blocks or bone block assemblies of the present invention.

FIGS. 8A-8D are views of one embodiment of an intermediate bone block of the present technology having gripping channels in the tissue engaging surface and a notched groove in the top surface. FIG. 8A is a side view of intermediate bone block 800, showing proximal end 801, distal end 802, tendon engaging surface 804, gripping channels 805 that traverse the width of the intermediate bone block, and top surface 803. FIG. 8B is a top view of intermediate bone block 800, showing proximal end 801, distal end 802, gripping channels 805 that traverse the width of the intermediate bone block, top surface 803, and notched groove 807. FIG. 8C is a perspective view of intermediate bone block 800, showing proximal end 801, gripping channels 805 that traverse the width of the intermediate bone block, gripping channels 806 that traverse the length of the intermediate bone block, top surface 803, and notched groove 807. FIG. 8D is an end view of intermediate bone block 800, showing proximal end 801, top surface 803 and notched groove 807. The cross-sectional profile of notched groove 807, as illustrated in FIG. 8D, is triangular.

FIGS. 9A-9G are end views of some embodiments of intermediate bone blocks having a stress concentrating feature in the form of a semi-circular notched groove. The end profiles of FIGS. 9A-9G correspond to the end profiles of FIGS. 6A-6G, with the addition of the notched groove. FIG. 9A is an end view of one embodiment of a intermediate bone block having a semi-circular end profile, having top surface 901, notched groove 902, and tendon engaging surface 903. FIG. 9B is an end view of one embodiment of a intermediate bone block having an end profile that is a circular segment less than a semi-circle, having top surface 904, notched groove 905, and tendon engaging surface 906. FIG. 9C is an end view of one embodiment of a intermediate bone block having an end profile that is a gibbous circular segment, or circular segment greater than a semi-circle, having top surface 907, notched groove 908, and tendon engaging surface 909. FIG. 9D is an end view of one embodiment of a intermediate bone block having an end profile that is a modified half octagon, having top surface 910, notched groove 911, and tendon engaging surface 912. FIG. 9E is an end view of one embodiment of a intermediate bone block having an end profile that is half of a dodecagon or a modified dodecagon, having top surface 913, notched groove 914, and tendon engaging surface 915. FIG.

9F is an end view of one embodiment of a intermediate bone block having a triangular end profile, having top surface 916, notched groove 917, and tending engaging surface 918. In the embodiment of FIG. 9F, the triangular profile is a right triangle, and the notched groove 917 is located where the right angle would otherwise be. FIG. 9G is an end view of one embodiment of a intermediate bone block having a rectangular end profile, having top surface 919, notched groove 920, and tendon engaging surface 921.

FIGS. 10A-10E are end views of some embodiments of intermediate bone blocks of the present technology having a stress concentrating feature in the form of a notched groove or truncation in the top surface. The end profile of the intermediate bone blocks in each of FIGS. 10A-10F is a modified half octagon having top surface 1001 and tendon engaging surface 1002. FIG. 10A is an end view of one embodiment of a intermediate bone block without a notch or truncation therein. FIG. 10B is an end view of one embodiment of a intermediate bone block having a semi-circular notched groove 1003 in top surface 1001. FIG. 10C is an end view of one embodiment of an intermediate bone block a "V" shaped notch 1004 in top surface 1001. FIG. 10D is an end view of one embodiment of a intermediate bone block having a rectangular notch 1005 in top surface 1001. FIG. 10E is an end view of one embodiment of a intermediate bone block having a truncation 1006 in top surface 1001.

In some particularly preferred embodiments, an intermediate bone block is configured to separate in a predetermined manner during implantation of the implant into a patient. In at least one such embodiment, the intermediate bone block separates at a predetermined location upon engagement with an interference screw during implantation.

Figure 11C:
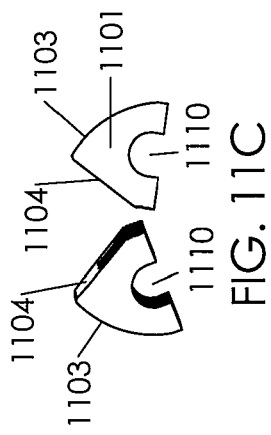
Figure 11B:
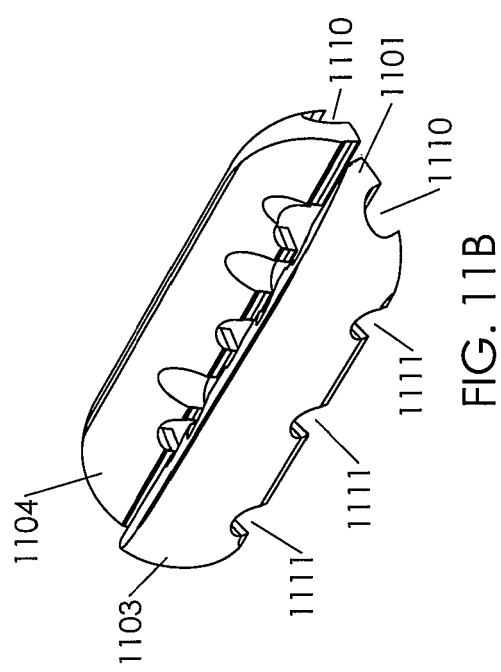
Figure 11A:
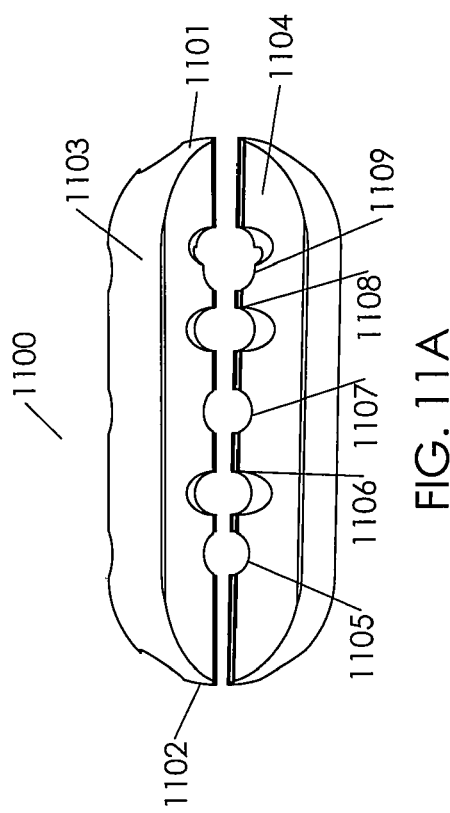

FIGS. 11A-11C illustrate one embodiment of a separated intermediate bone block 1100. Prior to implantation, intermediate bone block 1100 would be a single piece, having a "V" shaped notched groove in the top surface and gripping channels in the tendon engaging surface. During implantation, intermediate bone block 1100 would separate into two halves in the manner illustrated in FIGS. 11A-11C. FIG. 11A is a top view of intermediate bone block 1100 after separation, showing proximal end 1101, distal end 1102, top surface 1103, notched groove 1104, and though-holes 1105, 1106, 1107, 1108, and 1109. In on embodiment, through holes 1105 and 1107 can be configured to accept a biocompatible connector, preferably a pin comprising cortical bone, to hold the graft together and to fix the bone block assembly at a location along the length of the tendon. In this same embodiment, through hole 1106 may be configured to accept a suture or multiple sutures, allowing the surgeon to more easily manipulate the graft during implantation and fixation. FIG. 11B is a perspective view of intermediate bone block 1100 after separation, showing proximal end 1101, top surface 1103, notched groove 1104, two gripping channels 1110 traversing the length of the intermediate bone block, and three gripping channels 1111 traversing the width of the intermediate bone block. FIG. 11C is an end view of intermediate bone block 1100 after separation, showing proximal end 1101, top surface 1102, notched groove 1104 and gripping channels 1110 that traverse the length of the intermediate bone block. In the view shown in FIG. 11C, the two halves of the separated intermediate bone block are shown, with each side of the original "V" of notched groove 1104 being on one half of the separated intermediate bone block.

In an alternative embodiment, one or more demineralized bone pin(s) may be used to hold the intermediate bone blocks secure along the length of the tendon until implantation, whereafter the demineralized pin may allow flexing, compression, or movement of the intermediate bone block to achieve a second grip or fresh bite on the tendon after implantation.

Figure 12B:
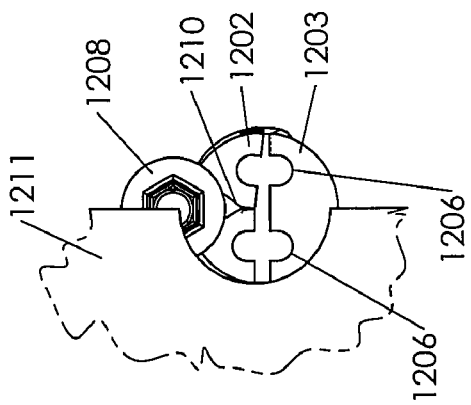
FIGS. 12A and 12B are views of one embodiment of a separated intermediate bone block of the present technology implanted into the bone tunnel of a patient with an interference screw.
Figure 12A:
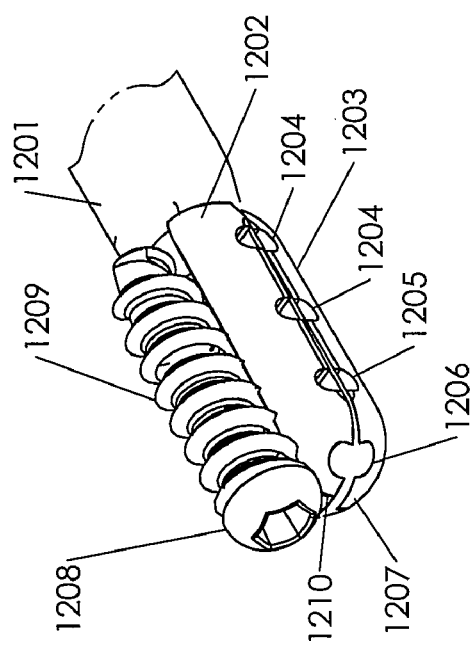

FIGS. 12A-12B illustrate one embodiment of a BTB of the present technology having an intermediate bone block that separates during implantation of the implant into a patient. FIG. 12A illustrates a perspective view of one end of the BTB implant, showing part of tendon 1201 having an end that is secured between intermediate bone block 1202 and intermediate bone block 1203. The bone block assembly further has distal end 1207. Intermediate bone blocks 1202 and 1203 each have gripping channels on their tendon engaging surfaces. Gripping channels 1204 and 1205 traverse the width of the intermediate bone blocks, and gripping channels 1206 traverse their length. In, the embodiment shown in the FIG. 12A, the first gripping channel across the width 1205 is substantially equivalent to the remaining gripping channels across the width 1204. In certain other embodiments, gripping channels may be of the same or different configurations, either across the width or along the length of the intermediate bone block. An interference screw 1208 having threads 1209 is illustrated as it would be inserted against the bone block assembly to fixate the BTB in a bone tunnel. Separation 1210 is shown in intermediate bone block 1202 underneath interference screw 1208. FIG. 12B is an end view of the illustrated BTB implant, showing a cut away of half of bone tunnel 1211 into which the implant has been inserted. FIG. 12B shows the bone block assembly comprising first intermediate bone block 1202 and second intermediate bone block 1203, each having gripping channels 1206 in their respective tendon engaging surfaces. First intermediate bone block 1202 has separation 1210 therein. As illustrated, interference screw 1208 has been inserted into bone tunnel 1211 with the bone block assembly. As illustrated, the bone tunnel is smaller in diameter than the combined width of the interference screw and the bone block assembly. Interference screw 1208 and the bone block assembly are each shown as being at least partially embedded in the bone surrounding the bone tunnel of the patient.

In some additional embodiments of the present technology that provide an altering of the geometric configuration of one or more of the intermediate bone blocks that form the bone block assembly, at least one intermediate bone block comprises cancellous bone. Accordingly, in at least one embodiment the present technology provides an implant comprising a tendon having a length, and a bone block assembly comprising at least two shaped dense cancellous intermediate bone blocks. The tendon is preferably secured between the first intermediate bone block and the second intermediate bone block at a fixed location along its length, and at least one of the first intermediate bone block or the second intermediate bone block has a first geometric configuration prior to implantation of the implant into a patient and a second geometric configuration after implantation of the implant into a patient.

Figure 13C:
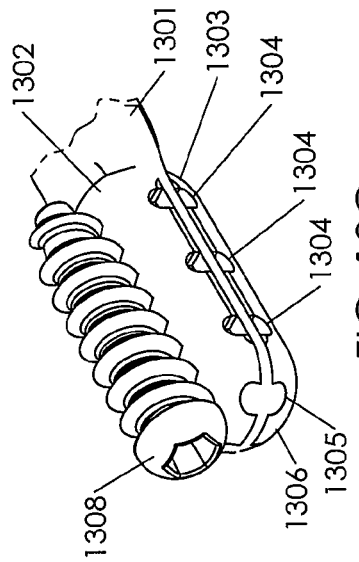
FIGS. 13A-13D are views of one end of one embodiment of an implant of the present technology that is implanted into the bone tunnel of a patient with an interference screw.
Figure 13D:
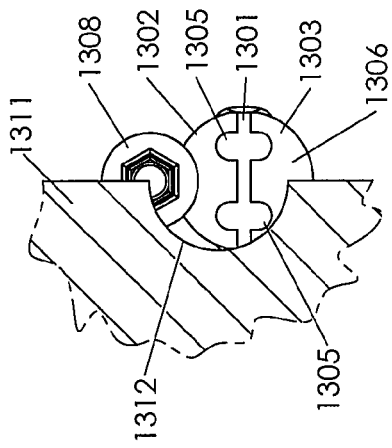
Figure 13B:
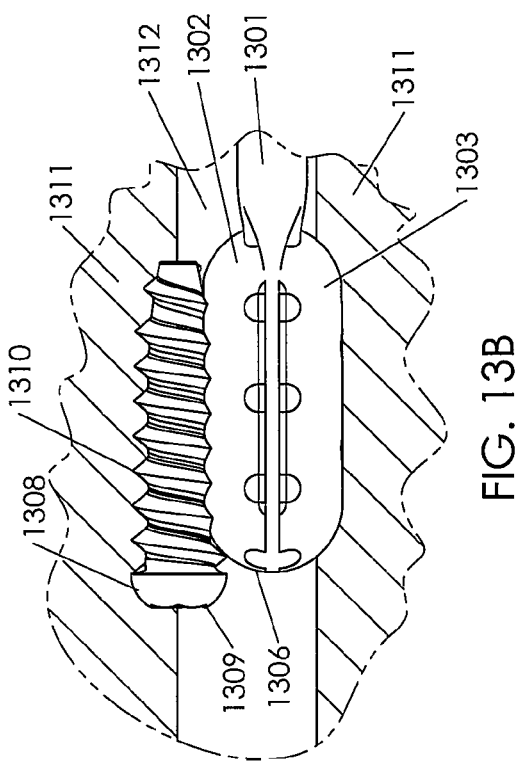
Figure 13A:
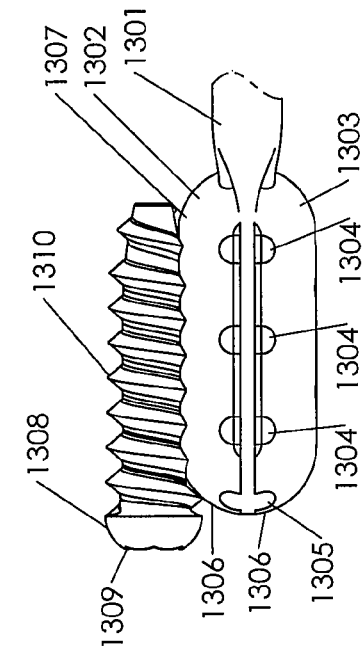

Due to the structural nature of cancellous bone, the geometric configuration of an intermediate bone block made therefrom can be altered by crushing, crunching, or compressing the intermediate bone block during implantation of the BTB into a patient. FIGS. 13A-13D illustrate one example of such an embodiment. FIG. 13A illustrates a side view of one end of a BTB implant of the present technology, showing part of tendon 1301 having its end secured between intermediate bone blocks 1302 and 1303 of the bone block assembly. Each of intermediate bone blocks 1302 and 1303 have a distal end 1306, and gripping channels 1304 and 1305 in their tendon engaging surfaces. Intermediate bone block 1302 has top surface 1307 that has been crushed and compressed by interference screw 1308. Interference screw 1308 has head 1309 and threads 1310. FIG. 13B illustrates a side view of one end of a BTB implant of the present technology in the context of the patient's bone 1311 and bone tunnel 1312. As illustrated, the bone tunnel 1312 is smaller in diameter than the combined width of the interference screw 1308 and the bone block assembly. Interference screw 1308 and the bone block assembly are each shown as being at least partially embedded in the bone surrounding the bone tunnel of the patient, with the top surface of intermediate bone block 1302 being crushed and compressed by interference screw 1308. FIG. 13C is a perspective view of one end of a BTB implant of the present technology, showing tendon 1301, intermediate bone blocks 1302 and 1303 of the bone block assembly, distal end 1306, and gripping channels 1304 and 1305 in their tendon engaging surfaces. FIG. 13D is an end view of a BTB implant of the present technology in the context of the patient's bone 1311 and bone tunnel 1312, showing intermediate bone blocks 1302 and 1303 of the bone block assembly with the end of tendon 1302 being sandwiched and secured therebetween. Just as in FIG. 13B, the illustration in 13D shows that the bone tunnel 1312 is smaller in diameter than the combined width of the interference screw 1308 and the bone block assembly, and that interference screw 1308 and bone block assembly are each at least partially embedded in the bone surrounding the bone tunnel of the patient, with the top surface of intermediate bone block 1302 being crushed and compressed by interference screw 1308.

Methods of Making BTBs of the Present Technology

BTB implants of the present technology can be made in any manner that results in an implant suitable for implantation into a patient.

For example, with respect to BTBs of the present technology comprising a tendon having a naturally attached bone component, one method of making an implant comprises the steps of providing a portion of a calcaneus bone having a natural attachment to an Achilles' tendon, separating the portion of a calcaneus bone into at least two pieces, and separating the Achilles' tendon into at least two sections by tearing the tendon along its fiber direction. In such embodiments of the present technology, the natural attachment to the Achilles' tendon is maintained on each piece of calcaneus bone when the bone is separated into pieces, and each section of the Achilles' tendon maintains a natural attachment to one piece of calcaneus bone when the tendon is separated. Preferably, the Achilles' tendon has a free end opposite the natural attachment and a length of at least about 50 mm from the natural attachment to the free end.

In some embodiments, the method further comprises the step of securing a bone component to the free end of the tendon. In other embodiments, the method further comprises securing a bone block assembly to the free end of the tendon. The step of securing a bone block assembly to the free end of the tendon can comprise providing a first intermediate bone block and a second intermediate bone block, compressing the free end of the tendon between the first intermediate bone block and the second intermediate bone block, and securing the tendon between the first intermediate bone block and the second intermediate bone block with at least one biocompatible connector, preferably a pin comprising cortical bone.

As another example, with respect to BTB implants of the present technology having a bone block assembly at each end thereof, a method for making an implant can comprise the steps of providing a tendon having a length of at least about 50 mm, wherein the tendon comprises along its length at least a first end, a first intermediate section, a central section, a second intermediate section, and a second end; securing a bone block assembly at the first end or the first intermediate section of the tendon; and securing a second bone block assembly at the second end or the second intermediate section of the tendon.

In some embodiments, a bone block assembly is secured to the tendon by stacking a first intermediate bone block into an assembly fixture with its tendon engaging surface facing upward, then placing an end or intermediate section of a tendon into the fixture on top of the tendon engaging face, followed by stacking a second first intermediate bone block into the fixture such that its tendon engaging surface engages the tendon. The assembly fixture can then be tightened or clamped to hold the pieces in juxtaposition while at least one biocompatible connector is inserted into a set of aligned through-holes in the intermediate bone blocks such that it passes through the tendon and pass substantially through each intermediate bone block. In embodiments where the biocompatible connectors are pins, the pins are preferably inserted so that the ends of the pins are flush with the outer surface of each intermediate bone block into which they are inserted. It is acceptable, however, for the ends of a pin to be slightly above or slightly below the outer surface of one or more intermediate bone blocks into which the pin is inserted.

Examples

Sample BTB implants were made and tested in accordance with the following procedures:

Static Testing: (Test Substrate: porcine tibias)

All static testing was conducted on an Instron testing machine. Each Sample BTB implant was statically pretensioned for 15 minutes to 90 N at three, 5 minute intervals. Each Sample BTB implant was dynamically preconditioned after the specimen had been pretensioned. The Sample BTB implant was relaxed to 30N for 30 seconds and then preconditioned for 15 cycles from 30N to 150N at 1 Hz. Immediately following dynamic preconditioning the specimen was pulled to failure at a rate of 50 mm/min.

During static pretensioning, data was recorded for load in Newtons and displacement in mm at an interval of 2N or every 1 second. During dynamic preconditioning and pull to failure, data was collected at an interval of 2N or every 0.05 seconds.

Dynamic Test: (Test Substrate: 20 lb/ft^3 Structural Foam, Sawbones Catalog Number 1522-03, Pacific Research Laboratories, Inc., Vashon, Wash.)

All dynamic testing was conducted in a chamber of distilled water at 37° C. on an MTS testing machine. Each Sample BTB implant was allowed to equilibrate in the chamber for 10 minutes, after which the graft was tensioned to 90N and held for 25 minutes in displacement control. The machine adjusted the tension after 5 minutes and 15 minutes to maintain the 90N. After the 25 minutes of tensioning, the machine unloaded the Sample BTB implant to 30N for one minute. Next, the Sample BTB implant was cycled for 1000 cycles between 50 and 250N and then tested to failure at a rate of 50 mm/min.

Test Results

Sample BTB implants 1-9 each had a bone block assembly with two intermediate bone blocks having the tendon sandwiched therebetween. In Samples 1-9, each intermediate bone block had a layer of cortical bone on the outer surface, and comprised dense cancellous bone at the tendon engaging surface. The results of the testing for Samples 1-9 are described in Table 1, below.

TABLE 1

| Sample | Test Method | Failure Load (Newtons) | Stiffness (Newtons/mm) | Notes |
|---|---|---|---|---|
| 1 | Static | 918.2 | 163.2 | 9 mm screw. Lost tension |
| 2 | Dynamic | 593.4 | 156.5 | Bone block in front pin on screw side cracked off |
| 3 | Dynamic | 551.8 | 176.8 | Made earlier |
| 4 | Dynamic | 781.5 | 206.7 | Very tight screw insertion |
| 5 | Dynamic | 635.3 | 161.3 | — |
| 6 | Dynamic | 686.5 | 191.4 | — |
| 7 | Dynamic | 673.8 | 181.3 | Screw rolled off and separated bone blocks |
| 8 | Dynamic | 779.7 | 228.5 | Very tight screw insertion, Bone block in front pin on screw side cracked off |
| 9 | Dynamic | 532.6 | 138.4 | Made earlier, Top bone block pushed out a little bit but did not break off, small crack appeared in foam during screw insertion. |

The average stiffness for Sample BTB implants 1-9 was 178.2 N/mm, with the lowest stiffness being Sample BTB implant 9 at 138.4 N/mm, and the highest stiffness being Sample 8 at 228.5 N/mm. The average load at failure was 683.6 N, with the lowest load being Sample BTB implant 9 at 532.6 N, and the highest being Sample BTB implant 1 at 918.2 N. Sample 1 was tested using the static test method. The highest load at failure for Samples tested using the dynamic test method was Sample BTB implant 4, at 781.5 N.

Sample BTB implants 10-14 each had a bone block assembly with two intermediate bone blocks having the tendon sandwiched therebetween. In Samples 10-14, one intermediate bone block had a layer of cortical bone on the outer surface, and comprised dense cancellous bone at the tendon engaging surface. The other intermediate bone block comprised entirely cancellous bone. The results of the testing for Samples 10-14 are described in Table 2, below.

TABLE 2

| Sample | Test Method | Failure Load (Newtons) | Stiffness (Newtons/mm) | Notes |
|---|---|---|---|---|
| 10 | Static | 662.5 | 169.4 | 7 mm screw |
| 11 | Static | 654.8 | 152.8 | 9 mm screw |
| 12 | Static | 452.9 | 162.9 | 9 mm screw |
| 13 | Dynamic | 607.2 | 230.5 | 7 mm screw in foam, inserted femorally |
| 14 | Dynamic | 510.1 | 285.4 | 7 mm screw in foam, inserted femorally, softer cancellous |

The average stiffness for Sample BTB implants 10-14 was 200.2 N/mm, with the lowest stiffness being Sample BTB implant 11 at 152.8 N/mm, and the highest stiffness being Sample 14 at 285.4 N/mm. The average load at failure was 577.5 N, with the lowest load being Sample BTB implant 12 at 452.9 N, and the highest being Sample BTB implant 10 at 662.5 N.

Sample BTB implants 15-21 each had a bone block assembly with two intermediate bone blocks having the tendon sandwiched therebetween. In Samples 15-21, each intermediate bone block comprised cortical bone. Each intermediate bone block had two gripping channels traversing the length and three gripping channels traversing the width of the tendon engaging surface. At least one intermediate bone block had a grooved notch on the outer surface with a "V" shaped cross sectional profile. The results of the testing for Samples 15-21 are described in Table 3, below.

TABLE 3

| Sample | Test Method | Failure Load (Newtons) | Stiffness (Newtons/mm) | Notes |
|---|---|---|---|---|
| 15 | Static | 614.6 | 139.3 | 9 mm screw. No crack |
| 16 | Static | 686.8 | 216.8 | 7 mm screw. Block split diagonal |
| 17 | Static | 280.9 | | 9 mm screw. Cracked. Soft tibia (half of block slid right out) |
| 18 | Static | 653.9 | 204.9 | 9 mm screw. No crack |
| 19 | Static | 439.4 | 96.6 | 7 mm screw. Broken w/9 mm screw first |
| 20 | Static | 597 | 141.3 | 9 mm screw. Cracked. Soft tibia (half of block slid right out) |
| 21 | Static | 377 | 175.8 | 9 mm screw. No crack. Soft reused tibia |

The average stiffness for Sample BTB implants 15-21 was 162.5 N/mm, with the lowest stiffness being Sample BTB implant 19 at 96.6 N/mm, and the highest stiffness being Sample 16 at 216.8 N/mm. The average load at failure was 521.4 N. Sample BTB implant 17 had a load failure at 280.9 N, which is lower than desired, but half of the block slid out. Sample BTB implant 21 had a load failure of 377 N, which is also lower than desired. Sample BTB implant 16 had the highest load failure, at 686.6 N.

While the present invention has been described above with reference to certain embodiments, it will be understood by those skilled in the art that various changes may be made, and equivalents may be substituted, without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. An implant comprising:
  a tendon having a length, wherein the tendon comprises along its length at least a first end, a first intermediate section, a central section, a second intermediate section, and a second end;
  and a bone block assembly comprising at least a first intermediate bone block and a second intermediate bone block;
  wherein the tendon is secured between the first intermediate bone block and the second intermediate bone block at a fixed location along its length at the first end or at the first intermediate section of the tendon; and
  wherein the bone block assembly has a first grip on the tendon prior to implantation of the implant into a patient and a second grip on the tendon after implantation of the implant into a patient; and
  wherein at least one of the first intermediate bone block or the second intermediate bone block comprises cancellous bone having a cortical cap or shell on at least one surface thereof; and
  further wherein at least one of the first intermediate bone block or the second intermediate bone block comprises a stress concentrating feature which is configured to separate in a predetermined manner during or after implantation of the implant into a patient; wherein the stress concentrating feature is formed by partially removing said cortical cap or shell from the center of said first intermediate bone block or said second intermediate bone block.

2. The implant of claim 1, wherein the first grip provides one level of compression to the tendon prior to implantation of the implant into a patient, and the second grip provides a second level of compression to the tendon after implantation of the implant into a patient.

3. The implant of claim 1, wherein the tendon is derived from a section of a whole tendon; wherein the whole tendon has a major direction along its length and the whole tendon comprises fiber bundles oriented in a fiber direction; wherein the fiber direction differs from the major direction of the whole tendon over at least a portion of the length of the whole tendon; and wherein the whole tendon is separated into sections along the fiber direction.

4. The implant of claim 1, wherein the first end of the tendon forms a tendon tail that extends beyond the first intermediate bone block and the second intermediate bone block when the tendon is secured between the first intermediate bone block and the second intermediate bone block at the first intermediate section of the tendon.

5. The implant of claim 1, wherein the first intermediate bone block and the second intermediate bone block each comprise allograft bone or xenograft bone.

6. The implant of claim 1, wherein both the first intermediate bone block and the second intermediate bone block comprise cancellous bone.

7. The implant of claim 1, wherein the first intermediate bone block and the second intermediate bone block are each allograft or xenograft bone blocks derived from a subchondral region of a long bone.

8. The implant of claim 1, wherein the first intermediate bone block comprises an outer surface and a tendon engaging surface, and the second intermediate bone block comprises an outer surface and a tendon engaging surface; and wherein the tendon engaging surface of at least one of the first intermediate bone block or the second intermediate bone block comprises a textured surface.

9. The implant of claim 8, wherein the textured surface comprises a natural texture of a cross section of the bone.

10. The implant of claim 8, wherein the textured surface comprises a machined texture selected from the group consisting of sawteeth, crosscut diamond peaks, ridges, gripping channels, gear grips, slots, and combinations thereof.

11. The implant of claim 10, wherein the textured surface comprises at least one gripping channel.

12. The implant of claim 1, wherein the first intermediate bone block comprises an outer surface and a tendon engaging surface; wherein the second intermediate bone block comprises an outer surface and a tendon engaging surface; and wherein the stress concentrating feature is located on the outer surface of at least one of the first intermediate bone block or the second intermediate bone block.

13. The implant of claim 1, wherein the first intermediate bone block comprises an outer surface and a tendon engaging surface; wherein the second intermediate bone block comprises an outer surface and a tendon engaging surface; and wherein the stress concentrating feature is located on the tendon engaging surface of at least one of the first intermediate bone block or the second intermediate bone block.

14. The implant of claim 1, wherein the first intermediate bone block and the second intermediate bone block each comprise at least one hole therein, wherein the at least one hole of the first intermediate bone block is aligned with the at least one hole of the second intermediate bone block, and wherein at least one biocompatible connector is inserted into the at least one hole of the first intermediate bone block and the second intermediate bone block.

15. The implant of claim 14, wherein the at least one biocompatible connector is a rigid pin comprising cortical bone, a metal, or a synthetic material.

16. The implant of claim 15, wherein the at least one rigid pin is a loose pin, a stepped pin, a reverse-tapered pin, a break-away pin, an asymmetric pin, a mismatched pin, or a demineralized pin.

17. The implant of claim 14, wherein the at least one biocompatible connector is a flexible connector comprising collagenous material, suture, biocompatible polymers, bioabsorbable polymers, bioabsorbable polymers, and bioresorbable polymers.

18. The implant of claim 14, wherein the at least one biocompatible connector is further inserted through the tendon between the first intermediate bone block and the second intermediate bone block.

19. The implant of claim 14, wherein the first intermediate bone block further comprises at least a second hole therein and the second intermediate bone block further comprises at least a second hole therein, wherein the second hole of the first intermediate bone block is aligned with the second hole of the second intermediate bone block, and wherein at least one biocompatible connector is inserted into the second hole of the first intermediate bone block and the second hole of the second intermediate bone block.

20. The implant of claim 14, wherein the first intermediate bone block and the second intermediate bone block each further comprise at least one graft manipulation hole therein, wherein the graft manipulation hole of the first intermediate bone block is aligned with the graft manipulation hole of the second intermediate bone block.

21. The implant of claim 1, further comprising at least a first bone component at the second end of the implant, wherein the first bone component has a naturally occurring attachment to the second end of the tendon.

22. The implant of claim 21, wherein the first bone component is derived from an allograft or xenograft calcaneus bone and the tendon is derived from an Achilles' tendon naturally attached to the calcaneus bone.

23. The implant of claim 21, further comprising a second bone component secured to the first bone component.

24. The implant of claim 23, wherein the second bone component comprises cancellous bone or cortical bone.

25. The implant of claim 23, wherein the second bone component is secured to the first bone component by at least one biocompatible connector.

26. The implant of claim 1, further comprising a second bone block assembly, wherein the second bone block assembly comprises at least a first intermediate bone block and a second intermediate bone block, and wherein the tendon is secured between the first inter mediate bone block and the second intermediate bone block of the second bone block assembly at the second end or at the second intermediate section of the tendon.

27. The implant of claim 26, wherein the tendon is secured between the first intermediate bone block and the second intermediate bone block of the first bone block assembly by at least one pin comprising cortical bone; and wherein the tendon is secured between the first intermediate bone block and the second intermediate bone block of the second bone block assembly by at least one pin comprising cortical bone.

28. The implant of claim 26, wherein the tendon and each of the bone block assemblies are derived from allograft or xenograft materials originating from a single donor, or from a biocompatible synthetic bone material.

29. The implant of claim 26, wherein each intermediate bone block comprises cancellous bone, cortical bone, both cancellous and cortical bone, or a biocompatible synthetic bone material.

30. The implant of claim 26, wherein each intermediate bone block comprises an outer surface and a tendon engaging surface, and wherein the tendon engaging surface of at least one intermediate bone block comprises textured surface.

31. The implant of claim 26, wherein the implant has a gauge length of from about 30 mm to about 55 mm.

32. The implant of claim 26, wherein each intermediate bone block is from about 15 mm to about 35 mm long and from about 1 mm to about 10 mm high.

33. The implant of claim 26, wherein the tendon is from about 9 mm to about 12 mm wide.

34. The implant of claim 1, further providing a cancellous bone channel which may readily accept an interference screw while concentrating stress to a break point along the center of said first intermediate bone block or said second intermediate bone block the intermediate bone block.

35. The implant of claim 1, wherein the first intermediate bone block or the second intermediate bone block is derived from the humeral or femoral head, femoral condyles, tibial plateau, dital tibia, talus, patella or vertebral bodies.

36. A method of forming the implant of claim 1 comprising the steps of:
providing a portion of a calcaneus bone having a natural attachment to an Achilles' tendon, wherein the Achilles' tendon has a free end opposite the natural attachment and a length of at least about 40 mm from the natural attachment to the free end; separating the portion of a calcaneus bone into at least two pieces, wherein the natural attachment to the Achilles' tendon is maintained on each piece of calcaneus bone; and
separating the Achilles' tendon into at least two sections along its fiber direction, wherein each section of the Achilles' tendon maintains a natural attachment to one piece of calcaneus bone and further comprising the step of securing a bone block assembly to the free end of the tendon, the bone block assembly comprising at least a first intermediate bone block and a second intermediate bone block; wherein the tendon is secured between the first intermediate bone block and the second intermediate bone block at a fixed locational along its length at a first end or at a first intermediate section of the tendon; and wherein the bone block assembly has a first grip on the tendon prior to implantation of the implant into a patient and a second grip on the tendon after implantation of the implant into a patient; and wherein at least one of the first intermediate bone block or the second intermediate bone block comprises cancellous bone having a cortical cap or shell on at least one surface thereof; and further wherein at least one of the first intermediate bone block or the second intermediate bone block comprises a stress concentrating feature which is configured to separate in a predetermined manner during or after implantation of the implant into a patient; wherein the stress concentrating feature is formed by partially removing said cortical cap or shell from the center of said first intermediate bone block or said second intermediate bone block.

37. The method of claim 36, wherein the step of securing a bone block assembly to the free end of the tendon comprises: providing the first intermediate bone block and the second intermediate bone block; compressing the free end of the tendon between the first intermediate bone block and the second intermediate bone block; and securing the tendon between the first intermediate bone block and the second intermediate bone block with at least one pin comprising cortical bone.

38. An implant comprising:
a tendon having a length, wherein the tendon comprises along its length at least a first end, a first intermediate section, a central section, a second intermediate section, and a second end;
at least a first bone component having a naturally occurring attachment to the first end of the tendon;
a bone block assembly comprising at least a first intermediate bone block and a second intermediate bone block; wherein the tendon is secured between the first intermediate bone block and the second intermediate bone block of the bone block assembly; and wherein the bone block assembly provides a first grip on the tendon prior to implantation and a second grip on the tendon after implantation; and
wherein at least one of the first intermediate bone block or the second intermediate bone block comprises cancellous bone having a cortical cap or shell on at least one surface thereof; and
further wherein at least one of the first intermediate bone block or the second intermediate bone block comprises a stress concentrating feature which is configured to separate in a predetermined manner during or after implantation of the implant into a patient; wherein the stress concentrating feature is formed by partially removing said cortical cap or shell from the center of said first intermediate bone block or said second intermediate bone block.

39. An assembled bone tendon bone implant comprising:
a tendon having a length and an effective diameter; and
a bone block assembly fixed along the length of the tendon, the bone block assembly comprising at least a first intermediate bone block and a second intermediate bone block, wherein the tendon is between the first intermediate bone block and the second intermediate bone block, and the first intermediate bone block and the second intermediate bone block are connected by at least one pin comprising cortical bone;
and wherein at least one of the first intermediate bone block or the second intermediate bone block comprises cancellous bone having a cortical cap or shell on at least one surface thereof; and
wherein the bone block assembly has an effective diameter of from about 9 mm to about 12 mm; wherein the effective diameter of the tendon is between about 80% and about 120% of the effective diameter of the bone block assembly; wherein the width of at least one of the first intermediate bone block or the second intermediate bone block is from about 8.5 mm to about 12 mm, the length of at least one of the first intermediate bone block or the second intermediate bone block is from about 15 mm to about 30 mm;
and the height of at least one of the first intermediate bone block or the second intermediate bone block is from about 3 mm to about 5 mm; and
further wherein at least one of the first intermediate bone block or the second intermediate bone block comprises a stress concentrating feature which is configured to separate in a predetermined manner during or after implantation of the implant into a patient; wherein the stress concentrating feature is formed by partially removing said cortical cap or shell from the center of said first intermediate bone block or said second intermediate bone block.

* * * * *